United States Patent
Hutcheson et al.

(10) Patent No.: US 10,107,823 B2
(45) Date of Patent: Oct. 23, 2018

(54) SYSTEM AND METHOD FOR STUDYING MATRIX VESICLE CALCIFICATION

(71) Applicant: THE BRIGHAM AND WOMEN'S HOSPITAL, INC., Boston, MA (US)

(72) Inventors: Joshua Daniel Hutcheson, Allston, MA (US); Elena Aikawa, Chestnut Hill, MA (US); Masanori Aikawa, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/035,901

(22) PCT Filed: Nov. 13, 2014

(86) PCT No.: PCT/US2014/065468
§ 371 (c)(1),
(2) Date: May 11, 2016

(87) PCT Pub. No.: WO2015/073679
PCT Pub. Date: May 21, 2015

(65) Prior Publication Data
US 2016/0291034 A1    Oct. 6, 2016

Related U.S. Application Data

(60) Provisional application No. 61/904,834, filed on Nov. 15, 2013.

(51) Int. Cl.
| | |
|---|---|
| *C12Q 1/02* | (2006.01) |
| *C12Q 1/00* | (2006.01) |
| *G01N 33/68* | (2006.01) |
| *G01N 33/84* | (2006.01) |

(52) U.S. Cl.
CPC ......... *G01N 33/6887* (2013.01); *G01N 33/84* (2013.01); *G01N 2333/78* (2013.01); *G01N 2500/20* (2013.01); *G01N 2800/323* (2013.01)

(58) Field of Classification Search
None
See application file for complete search history.

(56) References Cited

U.S. PATENT DOCUMENTS

| | | |
|---|---|---|
| 2005/0019836 A1 | 1/2005 | Vogel et al. |
| 2005/0271614 A1 | 12/2005 | Wolfinbarger, Jr. |
| 2007/0077267 A1 | 4/2007 | Molz, IV et al. |
| 2010/0185079 A1 | 7/2010 | Huizenga et al. |
| 2013/0101513 A1 | 4/2013 | Yang et al. |

OTHER PUBLICATIONS

Artym et al (Curr. Protoc. Cell Biol., 10.182:1-23 (2010).*
Chen et al., Kidney Inter., 77:436-442 (2010).*
D'Amore et al., Biomater., 31:5345-5354 (2010).*
Glimcher, Anatom. Rec., 224:139-153 (1989).*
Golub et al., Biochim. Biophys. Acta., 1790(12): 1592-1598 (2009).*
Li et al., Circ Res., 98:905-912 (2006).*
Mason et al., Acta Biomater., 9(1):4635-4644 (2013).*
Orbe et al., Atherosclerosis, 170:269-276 (2003).*
Sung et al., Biomater., 30(27):4833-4841 (2009).*
Thouverey et al., J. Cell. Biochem., 106:127-138 (2009).*
Chen et al., "Annexin-mediated matrix vesicle calcification in vascular smooth muscle cells," J. Bone Miner. Res. 23(11):1798-805 (2008).

* cited by examiner

*Primary Examiner* — Thomas J. Visone
(74) *Attorney, Agent, or Firm* — Nixon Peabody LLP

(57) ABSTRACT

Systems and methods for imaging of matrix vesicle-derived calcification are described. In one embodiment, the method comprises raising the pH of collagen stored in a solution, thereby causing the collagen to come out of the solution to form a network, adding matrix vesicles to the network, resulting in calcifications, and imaging the formation of the calcification. The calcification process can be imaged in real time by confocal or reflected light microscopy.

5 Claims, 18 Drawing Sheets

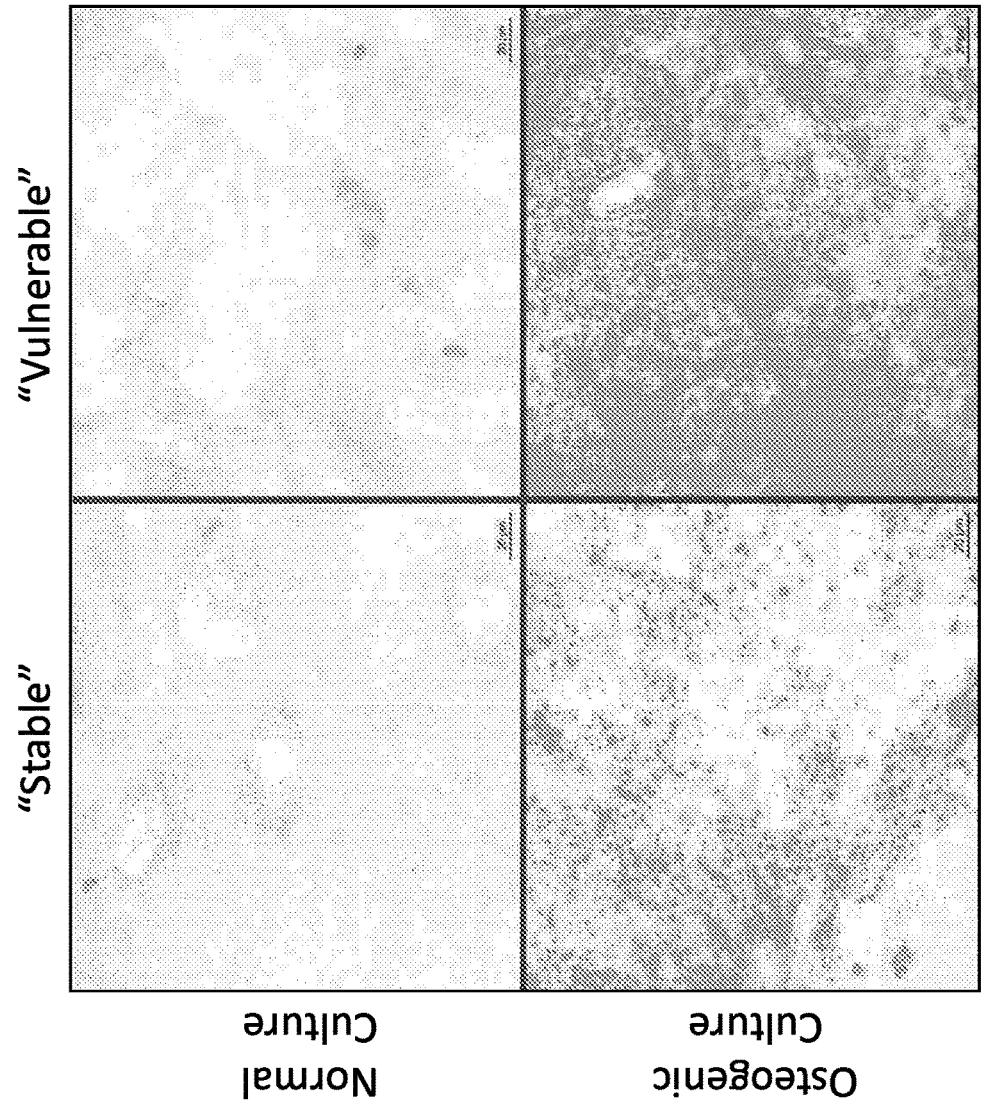

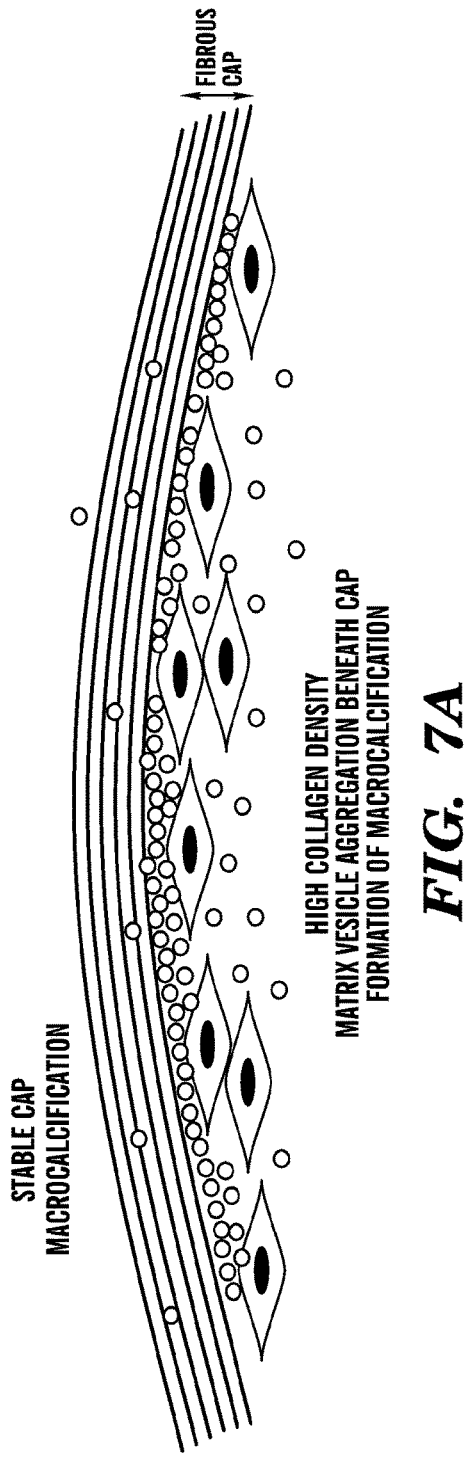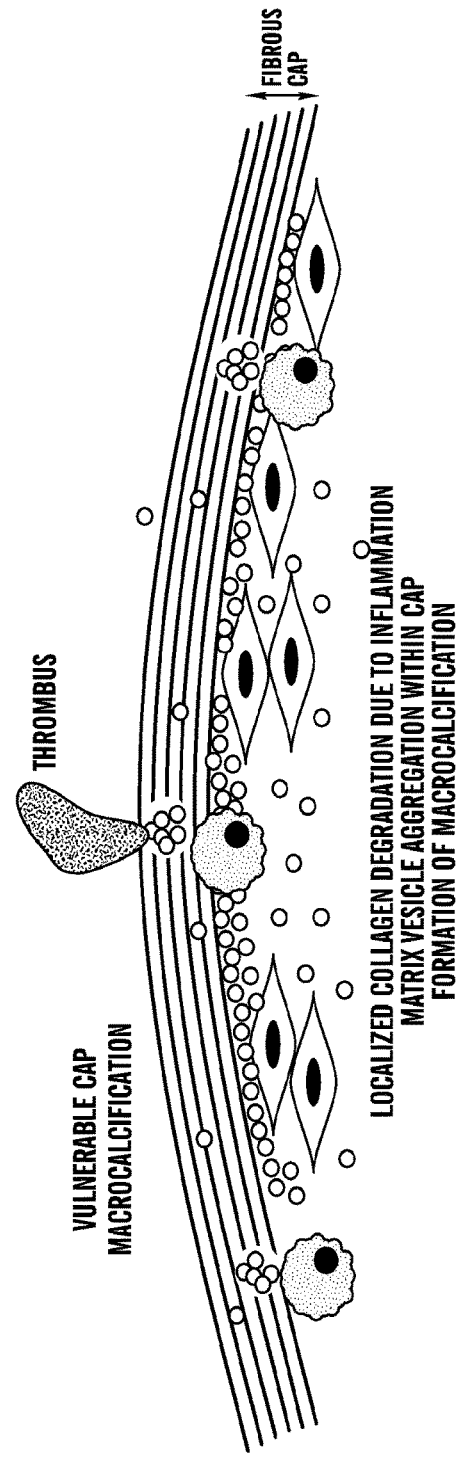

SYSTEM AND METHOD FOR STUDYING MATRIX VESICLE CALCIFICATION

CROSS REFERENCE TO RELATED APPLICATION

This application is a 35 U.S.C. § 371 National Phase Entry Application of International Application No. PCT/US2014/065468 filed Nov. 13, 2014, which designates the U.S. and which claims benefit under 35 U.S.C. § 119(e) of the U.S. provisional application No. 61/904,834 filed Nov. 15, 2013, the contents of which are incorporated herein by reference in their entirety.

FIELD

Embodiments of the disclosure relate to visualization, in particular, of a controllable three-dimension (3D) collagen hydrogel model for studying and imaging of extracellular matrix vesicles/exosomes calcification.

BACKGROUND

Rupture of "vulnerable" or "unstable" atherosclerotic plaques and subsequent vessel occlusion via thrombus formation is the leading cause of acute myocardial infarction and stroke. Classically, atherosclerotic plaque vulnerability has been attributed to a reduction in thickness of collagen in the atherosclerotic fibrous cap.

It has been identified that micro-calcifications in the collagenous fibrous cap contribute to biomechanical failure of arterial atherosclerotic plaques. Similar mechanisms appear to contribute to failures of other soft tissues due to ectopic calcification, including but not limited to vein graft failure (e.g., occlusive disease in vein grafts for peripheral arterial disease or coronary stenosis, occlusion or narrowing of AV fistulas or grafts for hemodialysis) and loss of tissue integrity of arotic valves, kidney, pancreas and liver. Calcifying matrix vesicles released by cells (e.g., smooth muscle cells, macrophages, valvular interstitial cells) within atherosclerotic plaque or other soft tissues contribute to the formation of micro-calcifications.

A major problem in the field that hinders research progress is the inability to identify and visualize the early processes that lead to micro-calcifications.

SUMMARY

Using embodiments of the claimed invention, it has been shown that aggregation of calcifying cell-derived matrix vesicles in collagen poor fibrous caps leads to the formation of micro-calcifications, a major contributor to atherosclerotic plaque instability and thrombosis. Thus, embodiments herein provide for controllable three-dimension (3D) collagen hydrogel systems and methods for imaging the formation of cell-derived matrix vesicle calcification. Such imaging can be used to determine how reagents modulate the growth of micro-calcifications.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

In one embodiment, provide herein is a method for the visualization of the formation extracellular matrix vesicle calcification is described. The visualization is primarily by imaging. The formation of the calcification is in vitro. The method comprises raising the pH of collagen stored in an acetic acid solution, thereby causing the collagen to come out of the acetic acid solution to form a network; adding cell-derived matrix vesicles to the network, resulting in micro and macro-calcifications; and imaging the formation of micro and macro-calcifications. The micro- and macro-calcifications can be imaged in real time. Dyes can be added to the micro-calcifications, thereby fluorescently labeling the matrix vesicles.

In one embodiment, provide herein is a method of producing matrix vesicle calcification, the method comprising raising the pH of collagen stored or prepared in an acidic solution, thereby causing the collagen to come out of the acidic solution to form a mesh-like network; and adding matrix vesicles to the collagen network, resulting in calcification.

In one embodiment, provide herein is a method for visualizing matrix vesicle calcification, the method comprising raising the pH of collagen stored or prepared in an acidic solution, thereby causing the collagen to come out of the acidic solution to form a mesh-like network, adding matrix vesicles to the collagen network, resulting in calcification, and imaging the calcification.

In one embodiment, provide herein is an in vitro calcification system comprising a 3D collagen hydrogel mesh-network to provide the platform support of calcification and cell-derived matrix vesicles that are overlaid on the network wherein the vesicles provide the initiation and/or materials for calcification. In one embodiment, the system further comprises an imaging system such as a microscope for visualization and capturing the calcification process. In another embodiment, the system further comprises further comprises a layer of cells upon which the 3D collagen hydrogel mesh-network is formed.

In one embodiment, provided herein is a composition comprising a 3D layer of collagen hydrogel mesh-network and cell-derived matrix vesicles that are overlaid on the network. In one embodiment, the composition further comprises a layer of cells beneath the collagen hydrogel mesh-network. In one embodiment, the composition further comprises a layer of calcification formed upon the mesh-network or therein or beneath. In one embodiment of the composition, the 3D collagen hydrogel mesh-network is produced by raising the pH of collagen stored or prepared in an acidic solution, thereby causing the collagen to come out of the acidic solution to form a mesh-like network In one embodiment, provided herein is a method of screening for agents that modulate the calcifications in unstable plaques comprising providing a collagen hydrogel/matrix vesicle calcification system, adding a test agent or a control test agent and imaging the calcification.

In one embodiment of the screening method described, the collagen hydrogel/matrix vesicle calcification system is produced by raising the pH of collagen stored or prepared in an acidic solution, thereby causing the collagen to come out of the acidic solution to form a mesh-like network; and adding matrix vesicles to the collagen network, thereby resulting in calcification.

In one embodiment of any method, system or composition described, the calcification is micro-, macro- or a combination of micro and macro calcifications.

In one embodiment of any method, system or composition described, the calcification is imaged in real time.

In one embodiment of any method, system or composition described, the calcifications are imaged in 3D.

In one embodiment of any method, system or composition described, the imaging is via confocal microscopy or reflected light microscopy.

In one embodiment of any method, system or composition described, the imaging comprises fluorescence.

In one embodiment of any method, system or composition described, the acidic solution of the collagen comprises acetic acid.

In one embodiment of any method, system or composition described, the acetic acid is about 0.1 M-about 0.5 M acetic acid.

In one embodiment of any method, system or composition described, the collagen is in a concentration range from about 0.1 mg/ml to about 5 mg/ml.

In one embodiment of any method, system or composition described, the concentration of the collagen is about 3.0 mg/ml to about 5.0 mg/ml.

In one embodiment of any method, system or composition described, the concentration of the collagen is about 0.1 mg/ml to about 3.0 mg/ml.

In one embodiment of any method, system or composition described, the collagen is selected from the group consisting of human collagen, bovine collagen or porcine collagen.

In one embodiment of any method, system or composition described, the collagen is selected from the group consisting of Type 1 collagen, Type II collagen, Type III collagen, Type IV collagen, or Type V collagen.

In one embodiment of any method, system or composition described, the collagen is a mixture of the group of collagen selected from Type 1, Type II, Type III, Type IV, and Type V collagen.

In one embodiment of any method, system or composition described, the collagen is human Type 1 collagen.

In one embodiment of any method, system or composition described, the pH of the collagen is raised to between about 7.0 and about 9.0.

In one embodiment of any method, system or composition described, the pH of the collagen is raised to 7.4.

In one embodiment of any method, system or composition described, the pH of the collagen is raised by adding an alkaline solution to the acidic collagen solution.

In one embodiment of any method, system or composition described, the alkaline solution is sodium or potassium hydroxide.

In one embodiment of any method, system or composition described, the matrix vesicles are prepared from smooth muscle cells, macrophages, valvular interstitial cells, fibroblasts, osteoblasts, mesenchymal stem cell, or any other cell that is known to deposit calcific mineral.

In one embodiment of any method, system or composition described, the matrix vesicles are labeled prior to adding to the collagen network.

In one embodiment of any method, system or composition described, the matrix vesicles are fluorescently labeled prior to adding to the collagen network.

In one embodiment, the method, system or composition further comprising adding dyes to the calcifications, thereby facilitating the visualization/imaging of the calcifications.

In one embodiment of any method, system or composition described, the dye is a fluorescent dye.

In one embodiment of any method, system or composition described, the fluorescent dye is a traditional or near-infrared fluorescent dye.

In one embodiment of any method, system or composition described, the dye labels the matrix vesicles added.

In one embodiment, the method, system or composition further comprising adding a reagent to the calcification to determine its effect on the calcifications.

In one embodiment of any method, system or composition described, the reagent is bisphosphonate.

In one embodiment of the screening method described, the collagen hydrogel/matrix vesicle calcification system is produced by raising the pH of collagen stored or prepared in an acidic solution, thereby causing the collagen to come out of the acidic solution to form a mesh-like network; and adding matrix vesicles to the collagen network, thereby resulting in calcification.

In one embodiment of the screening method described, the control test agent is a buffer or a cell culture medium.

In one embodiment of the screening method described, the modulation can be promoting calcification or inhibiting calcification.

In one embodiment, the screening method further comprising determining that the test agent is promoting calcification when calcification occurs faster/increased/improved compared to the control test agent.

In one embodiment, the screening method further comprising determining that the test agent is inhibiting calcification when calcification occurs slower/decreased/reduced compared to the control test agent.

In one embodiment of the screening method described, the faster or slower is at least 5% compared to the control test agent.

Definitions

As used herein, the term "matrix vesicles" when used in the context of micro- and macro-calcification described herein refers to the extracellular vesicles or exosomes of diameter of between 30 and 100 nm that are released from cells into the cell surrounding, e.g., all biological fluids, including blood, urine, and cultured medium of cell cultures. In the embodiments herein, the matrix vesicles facilitate mineral nucleation and the deposition of hydroxyapatite—the calcification process.

As used herein, matrix vesicles, extracellular matrix vesicles and cell-derived matrix vesicles are used interchangeably.

As used herein, the term "calcification" when used in the context of plaque calcification and vascular calcification refers to the process by which calcium phosphate mineral is deposited within a substance (tissue or collagen hydrogel model).

As used herein, the term "micro-calcification" when used in the context of plague calcification and vascular calcification refers to small calcifications that initially occur in atherosclerotic plaque that is less than 15 micrometers in diameter.

As used herein, the term "macro-calcification" when used in the context of plague calcification and vascular calcification refers to subsequent calcification following the formation of micro-calcification and it is larger than 15 micrometers in diameter.

As used herein, the term "agent" refers to any substance that can modulate the calcification. Examples of agents include, but are not limited to, small organic molecules, large organic molecules, small synthetic molecules, large synthetic molecules, amino acids, peptides, polypeptides, nucleotides, nucleic acids (including DNA, cDNA, RNA, antisense RNA and any double- or single-stranded forms of nucleic acids), polynucleotides, carbohydrates, lipids, lipoproteins, glycoproteins, inorganic ions (including, for example, Gd3+, lead and lanthinum).

In one embodiment, the term "agent" refers to any entity that is normally not present or not present at the levels being administered to a cell, tissue or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, "modulate" or "modulation" with reference to calcification refers to any changes in the rate and/or amount of deposition of calcium salts and/or hydroxyapatite including but not limited to the texture, structure, topography, strength and deformability of the deposited material. Modulation includes, for example, increases, up-regulation, induction, stimulation, potentiation, relief of inhibition, reduction, inhibition, down-regulation, decreases and suppression.

As used herein, the term "prevent" or "prevention" refers to stopping, hindering, and/or slowing down the onset and/or development of calcification in the calcification systems described. In one embodiment, prevent is synonymous with inhibit.

As used herein, the term "inhibit" or "inhibition" means the reduction or prevention of the deposition of hydroxyapatite or calcification.

In one embodiment, inhibition includes slowing the rate of the deposition of hydroxyapatite or calcification. The calcification rate can be reduced by about 5%, about 10%, about 15%, about 20%, about 30%, about 40%, about 50%, about 60%, about 70%, about 80%, about 90%, about 100%, about 125%, about 150% or more compared to the calcification rate obtained in the presence of a control test agent.

In another embodiment, inhibition also means a reduction in the size of the calcified deposit of about 5%, at least 10%, about 15%, at least 20%, at least 30%, at least 40%, at least 50%, at least 60%, at least 70%, at least 80%, at least 90%, up to and including 100% when compared to the calcification deposit obtained in the presence of a control test agent.

As used herein, the term "promote" and "promotion" when used in the context of the calcification described herein refers to furthering the progress, support or actively encourage the calcification.

In one embodiment, promotion includes increasing the rate of the deposition of hydroxyapatite or calcification when compared to the calcification rate obtained in the presence of a control test agent. The increased can be by about 5%, at least 10%, about 15%, at least 20%, at least 30%, at least 40%, at least 50%, at least 60%, at least 70%, at least 80%, at least 90%, up to and including 100% or more when compared to the calcification rate obtained in the presence of a control test agent.

In another embodiment, promotion includes increasing the size of the calcification deposit obtained when compared to the calcification obtained in the presence of a control test agent. The increased can be by about 5%, at least 10%, about 15%, at least 20%, at least 30%, at least 40%, at least 50%, at least 60%, at least 70%, at least 80%, at least 90%, up to and including 100% when compared to the calcification deposit obtained in the presence of a control test agent.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used herein, the term "vector" refers broadly to any plasmid, phagemid or virus encoding an exogenous nucleic acid. The term is also be construed to include non-plasmid, non-phagemid and non-viral compounds which facilitate the transfer of nucleic acid into virions or cells, such as, for example, poly-lysine compounds and the like. The vector may be a viral vector that is suitable as a delivery vehicle for delivery of the nucleic acid, or mutant thereof, to a cell, or the vector may be a non-viral vector that is suitable for the same purpose. Examples of viral and non-viral vectors for delivery of DNA to cells and tissues are well known in the art.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 2B illustrates a stable cap model and vulnerable cap model for a normal culture and an osteogenic culture. The stable cap model led to an increase in calcification beneath the collagen hydrogels compared to the, while micro-calcifications were found within the cap in the vulnerable cap model. Invented images are shown.

FIG. 7A illustrates a stable fibrous cap with high collagen density.

FIG. 7B illustrates a vulnerable fibrous cap with localized collagen degradation. This 3D model has led us to a new unifying hypothesis of plaque vulnerability. Formation of microcalcifications (new instability criteria) is inseparable from a reduction of collagen within the fibrous cap (traditional instability criteria).

DETAILED DESCRIPTION

Figure 1A:
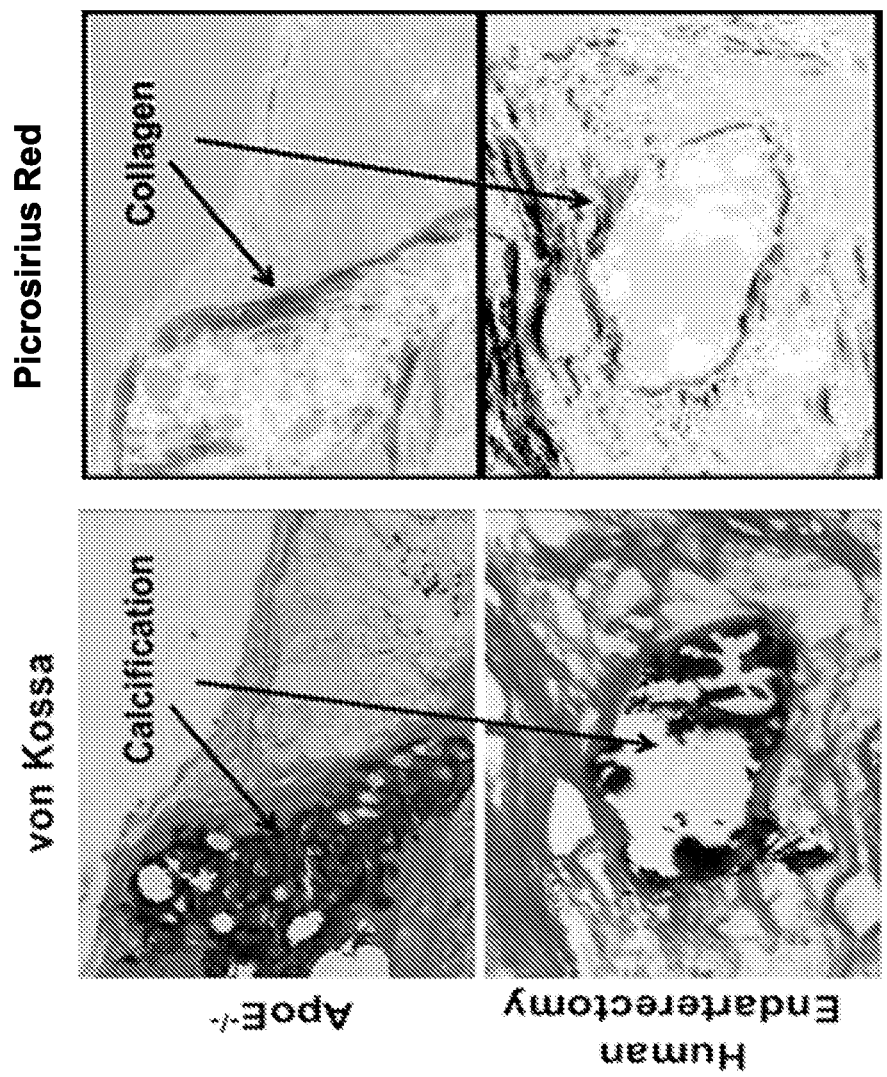
FIG. 1A illustrates calcifications and collagen in mouse and human arteries. Invented fluorescent images show Picrosirius red staining of collagen.

Systems and methods for imaging and for the visualization of the formation extracellular of matrix vesicle calcification are described. In the following description, for purposes of explanation, numerous specific details are set forth in order to provide a thorough understanding of the exemplary embodiments. It is apparent to one skilled in the art, however, that the present disclosure can be practiced without these specific details or with an equivalent arrangement.

An embodiment of the claimed method produces a hydrogel that allows for the real time imaging of cell-derived extracellular matrix vesicle calcification. Collagen stored in an acidic solution is diluted to a particular starting concentration depending on the processes that are to be performed thereon. For example, as discussed further herein, solutions with a high density of collagen can be used to simulate a stable fibrous cap, while solutions with a low density of collagen can be used to simulate a vulnerable fibrous cap. In one embodiment, the acidic solution is acetic acid; however, any acid may be used with a pH between 2 and 5.

Next, the pH of the collagen acidic solution is slowly raised. In one example, the pH is raised to 7.4 by slowly adding 5N NaOH to the collagen solution. At the higher pH, the collagen comes out of the solution to form fibers, resulting in a mesh-like network in the form of a hydrogel. Media is collected from cells (e.g., smooth muscle cells) kept under controlled culture conditions, and matrix vesicles derived from the media are added to the collagen network. The matrix vesicles facilitate mineral nucleation and the deposition of hydroxyapatite—the calcification process. The resulting calcification processes within the hydrogel are imaged. The calcifications can be imaged, for example, by confocal reflection microscopy or fluorescent time-lapse microscopy, the latter of which can be used if the matrix vesicles have been stained with a fluorescent dye, as discussed further herein. This system allows for the visualization of the formation of micro-calcifications and/or macro-calcification in real-time.

Accordingly, provided herein is a method for producing a calcification system, the method comprising: (a) raising the pH of collagen stored or prepared in an acidic solution, thereby causing the collagen to come out of the acidic solution to form a mesh-like network; and (b) adding cell-derived matrix vesicles to the collagen network thereby resulting in calcification.

In another embodiment, provided herein is a method for studying via imaging matrix vesicle calcification or for the visualization of the formation extracellular of matrix vesicle calcification, the method comprising: (a) raising the pH of collagen stored or prepared in an acidic solution, thereby causing the collagen to come out of the acidic solution to form a mesh-like network; (b) adding cell-derived matrix vesicles to the collagen network thereby resulting in calcification; and (c) imaging the calcification.

In one embodiment of the method described, the method further comprises providing a solution of collagen wherein the collagen is solubilized in an acidic solution.

In one embodiment, provide herein is an in vitro calcification system comprising a 3D collagen hydrogel mesh-network to provide the platform support of calcification and cell-derived matrix vesicles that are overlaid on the network wherein the vesicles provide the initiation and/or materials for calcification. In one embodiment, the system further comprises at least one imaging equipment such as a microscope for visualization and capturing the calcification process. In another embodiment, the system further comprises a computer, a display monitor and associated storage device. In another embodiment, the system further comprises a layer of cells upon which the 3D collagen hydrogel mesh-network is formed.

In one embodiment of the system, the collagen hydrogel mesh-network is produced by raising the pH of an acidic collagen solution to at least pH 7.0. In another embodiment, the pH of an acidic collagen solution is raised to between pH 7.0 to 9.0. In other embodiments, the pH of an acidic collagen solution is raised to about 7.1, 7.2, 7.3, 7.4, 7.5, 7.6, 7.7, 7.8, 7.9, 8.0, 8.1, 8.2, 8.3, 8.4, 8.5, 8.6, 8.7, 8.9 or 9.0.

In one embodiment of any method or system described, the calcification comprises micro-calcification, macro-calcification or a combination of micro- and macro-calcifications.

In one embodiment of any method or system described, the calcification is imaged in real time.

In one embodiment of any method or system described, the calcifications are imaged in 3D.

In one embodiment of any method or system described, the imaging is via confocal microscopy or reflected light microscopy.

In one embodiment of any method or system described, the imaging comprises fluorescence.

In one embodiment of any method or system described, the acidic solution of the collagen comprises acetic acid.

In one embodiment of any method or system described, the acetic acid is about 0.1 M-about 0.5 M acetic acid. In other embodiments, the concentration of the acetic acid is about 0.15, 0.2, 0.25, 0.3, 0.35, 0.4, or 0.45 M, including all the concentrations to the second decimal place between about 0.1 M-about 0.5 M.

In one embodiment of any method or system described, the collagen is in a concentration range from about 0.1 mg/ml to about 5 mg/ml. In other embodiments, the concentration of the acidic solution of collagen is about 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, or 5.0 mg/ml, including all concentrations to the second decimal place between about 0.1 mg/ml-about 5 mg/ml.

In one embodiment of any method or system described, a high concentration of collagen is used to produce a mesh-network with a stable cap. In one embodiment, the high concentration of collagen is about 3.0 mg/ml to about 5.0 mg/ml. In other embodiments, the high concentration of collagen used to produce a mesh-network with a stable cap is about 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, or 5.0 mg/ml, including all the concentrations to the second decimal place between about 3.0 mg/ml-about 5 mg/ml.

In one embodiment of any method or system described, the concentration of the collagen is about 3.0 mg/ml to about 5.0 mg/ml.

In one embodiment of any method or system described, a lower concentration of collagen is used to produce a mesh-network with an unstable cap. In one embodiment, the low concentration of collagen is about 0.1 mg/ml to about 3.0 mg/ml. In other embodiments, the high concentration of collagen used to produce a mesh-network with a stable cap is about 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0 mg/ml, including all the concentrations to the second decimal place between about 0.1 mg/ml-about 3.0 mg/ml.

In one embodiment of any method or system described, the concentration of the collagen is about 0.1 mg/ml to about 3.0 mg/ml.

In one embodiment of any method or system described, the collagen is selected from the group consisting of human collagen, bovine collagen or porcine collagen.

In one embodiment of any method or system described, the collagen is selected from the group consisting of Type 1 collagen, Type II collagen, Type III collagen, Type IV collagen, or Type V collagen.

In one embodiment of any method or system described, the collagen is a mixture of the group of collagen selected from Type 1, Type II, Type III, Type IV, and Type V collagen.

In one embodiment of any method or system described, the collagen is human Type 1 collagen.

In one embodiment, the pH of the collagen is raised to between about 7.0 and about 9.0. In other embodiments, the pH of the collagen is raised to about 7.1, 7.2, 7.3, 7.4, 7.5, 7.6, 7.7, 7.8, 7.9, 8.0, 8.1, 8.2, 8.3, 8.4, 8.5, 8.6, 8.7, 8.9 or 9.0.

In one embodiment of any method or system described, the pH of the collagen is raised to about 7.4 or 7.5.

In one embodiment of any method or system described, the pH of the collagen is raised by adding an alkaline solution to the acidic collagen solution.

In one embodiment of any method or system described, the alkaline solution is sodium or potassium hydroxide.

In one embodiment of any method or system described, the collagen mesh-network is formed over a layer of cells. For example, smooth muscle cells, macrophages, fibroblasts, osteoblasts, mesenchymal cells, valvular interstitial or endothelial cells or any other cell that is known to deposit calcific mineral are cultured on a cover-glass.

In one embodiment of any method or system described, the matrix vesicles are prepared from smooth muscle cells, macrophages, valvular interstitial cells, fibroblasts, osteoblasts, mesenchymal stem cell, or any other cell that is known to deposit calcific mineral.

In one embodiment of any method or system described, the matrix vesicles are prepared from cells that have been transfected with a DNA construct or vector such that the transfected cells express proteins that are fluorescently labeled.

In one embodiment of any method or system described, the matrix vesicles are labeled prior to adding to the collagen network. For example, the matrix vesicles are incubated with a fluorescent dye for a period of time, separated from the free dye and then added to the collagen mesh-network.

In one embodiment of any method or system described, the matrix vesicles are fluorescently labeled prior to adding to the collagen network.

In one embodiment of any method or system described, further comprising adding dyes to the calcifications, thereby facilitating the visualization/imaging of the calcifications.

In one embodiment of any method or system described, the dye is a fluorescent dye.

In one embodiment of any method or system described, the fluorescent dye is a traditional or near-infrared fluorescent dye. Traditional fluorescent dyes such as Cell Tracker and Cell Trace dyes excite and emit light at 380 nm-700 nm wavelength. Near-infrared fluorescent dyes such as OsteoSense® emit light beyond the 700 nm wavelength.

In one embodiment of any method or system described, the dye labels the matrix vesicles added. For examples, dyes that label membranes or calcium can be used.

Matrix vesicles, the precursors of micro-calcifications, can be fluorescently labeled with dyes, such as cell tracer dyes, for added resolution and sensitivity. The dyes can be added directly to the media collected from the cells. Alternatively, the vesicles can be labeled by transducing cells with vectors to express fluorescently labeled proteins that are packaged into the vesicles. For example, calcium binding proteins and channels such as the family of annexins have been shown in calcifying matrix vesicles. Therefore, fluorescent versions of these proteins could be used to identify matrix vesicles. Methods of transducting cells with such vectors are known in the art. For examples, expression plasmids or vectors for fluorescently-labeled annexins are commercially available at EVROGEN (catalog # FP 321 and # FP414) and at ALLELEUSTRIOUS (catalog # ABP-FP-WAN1000 and # ABP-FP-TAN1000).

In this embodiment of any method or system described, the cells are transfected with a DNA construct wherein the construct comprises the genetic information for expressing a fluorescent fusion protein such that the transfected cell produce proteins that are fluorescently labeled.

In one embodiment of any method or system described, the matrix vesicles comprise fluorescently labeled proteins. For example, fluorescently labeled annexins and S100 proteins.

In one embodiment of any method described, the method further comprises adding a reagent to the calcifications to determine its effect on the calcifications.

In one embodiment of any method described, the reagent is bisphosphonate. In other embodiments, the agent is any known inhibitor (e.g., alkaline phosphatase inhibitor, fetuin A, ENPP1, etc.) or stimulator (e.g., calcium and/or phosphate; pro-inflammatory stimuli: S100A9, IL-1β, TGF-β, etc; pro-calcific stimuli: BMP2, NOTCH 1, etc.) of calcification.

Using this technique along with confocal reflection microscopy to identify the relationship between vesicles and near-infrared calcium tracer to monitor changes in matrix vesicle calcification, this 3D hydrogel imaging system can be used to test the ability of compounds to promote or prevent matrix vesicle aggregation and/or calcification. The near-infrared calcium tracer may be any fluorescent imaging agent, such as, for example, OsteoSense®.

This in vitro calcification system comprising collagen hydrogel/matrix vesicle provides a novel way to visualize and assay formation of micro-calcifications and changes in atherosclerotic plaque vulnerability. Matrix vesicle mediated calcification can be observed in real time. This leads to a better understanding of how to "stabilize" the plaque and/or prevent the plaque rupture, which can lead to thrombosis. This methodology can be also used to understand the formation of micro-calcifications in the calcific aortic valve disease, a condition that currently has no effective treatment except surgical valve replacement.

Accordingly, in one embodiment, provided herein is a method of screening for agent(s) that modulate the calcification in unstable plaques comprising providing a collagen hydrogel/matrix vesicle calcification system, adding a test agent or a control test agent to the system and imaging the calcification.

In one embodiment of the method described, the collagen hydrogel/matrix vesicle calcification system comprises raising the pH of collagen stored or prepared in an acidic solution, thereby causing the collagen to come out of the acidic solution to form a mesh-like network and adding matrix vesicles to the collagen network thereby resulting in calcifications.

In one embodiment of the method described, the control test agent is a buffer or cell culture media. In one embodiment of the method described, the buffer is that which the test agent is dissolved in. In one embodiment, the control test agent serves as the baseline or standard to which other test agent's ability to modulate the calcification process in the described system is measured, compared and evaluated.

In one embodiment of the method described, the modulation can be promoting calcification or inhibiting calcification.

In one embodiment of the method described, the method further comprising determining that the test agent is promoting calcification when calcification increases compared to that in the presence of the control test agent.

In one embodiment of the method described, the method further comprising determining that the test agent is inhibiting calcification when calcification decreases compared to that in the presence of the control test agent.

In one embodiment of the method described, the increase or decrease is at least 5% compared to the control test agent.

In some embodiments, the reduction or decrease is by about 5%, about 10%, about 15%, about 20%, about 30%, about 40%, about 50%, about 60%, about 70%, about 80%, about 90%, about 100%, about 125%, about 150% or more compared to that obtained in the presence of a control test agent.

In some embodiments, the increase is by about 5%, about 10%, about 15%, about 20%, about 30%, about 40%, about 50%, about 60%, about 70%, about 80%, about 90%, about 100%, about 125%, about 150% or more compared to that obtained in the presence of a control test agent.

In one embodiment, provided herein is a composition comprising a 3D layer of collagen hydrogel mesh-network and cell-derived matrix vesicles that are overlaid on the network. In one embodiment, the composition further comprises a layer of cells beneath the collagen hydrogel mesh-network. In another embodiment, the composition further comprises cell-derived matrix vesicles that are incorporated within the network.

In one embodiment of the composition described, the 3D layer of collagen hydrogel mesh-network is between about 0.1 μm to about 5 mm in thickness. In some embodiments, the thickness of the 3D layer of collagen hydrogel mesh-network is between about 0.1 μm to about 0.5 mm, about 0.1 μm to about 1 mm, about 0.1 μm to about 1.5 mm, about 0.1 μm to about 2 mm, about 0.1 μm to about 2.5 mm, about 0.1 μg to about 3 mm, about 0.1 μm to about 3.5 mm, about 0.1 μm to about 4 mm, about 0.1 μm to about 4.5 mm, about 0.5 μm to about 1 mm, about 0.5 μm to about 1.5 mm, about 0.5 μm to about 2 mm, about 0.5 μm to about 2.5 mm, about 0.5 μm to about 3 mm, about 0.5 μm to about 3.5 mm, about 0.5 μm to about 4 mm, about 0.5 μm to about 4.5 mm, about 1.0 μm to about 1.5 mm, about 1.0 μm to about 2 mm, about 1.0 μm to about 2.5 mm, about 1.0 μm to about 3 mm, about 1.0 μm to about 3.5 mm, about 1.0 μm to about 4 mm, about 1.0 μm to about 4.5 mm, about 1.5 μm to about 2 mm, about 1.5 μm to about 2.5 mm, about 1.5 μm to about 3 mm, about 1.5 μm to about 3.5 mm, about 1.5 μm to about 4 mm, about 1.5 μm to about 4.5 mm, about 2.0 μm to about 2.5 mm, about 2.0 μm to about 3 mm, about 2.0 μm to about 3.5 mm, about 2.0 μm to about 4 mm, about 2.0 μm to about 4.5 mm, about 2.5 μm to about 3 mm, about 2.5 μm to about 3.5 mm, about 2.5 μm to about 4 mm, about 2.5 μm to about 4.5 mm, 3.0 μm to about 3.5 mm, about 3.0 μm to about 4 mm, about 3.0 μm to about 4.5 mm, about 3.5 μm to about 4 mm, about 3.5 μm to about 4.5 mm, and about 4.0 μm to about 4.5 mm in thickness. In some embodiments, the thickness of the 3D layer of collagen hydrogel mesh-network is about 0.2 μm, 0.3 μm, 0.4 μm, 0.5 μm, 0.6 μm, 0.7 μm, 0.8 μm, 0.9 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm, 6.2 μm, 6.4 μm, 6.6 μm, 6.8 μm, 7.0 μm, 7.2 μm, 7.4 μm, 7.6 μm, 7.8 μm, 8.0 μm, 8.2 μm, 8.4 μm, 8.6 μm, 8.8 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 110 μm, 115 μm, 120 μm, 125 μm, 130 μm, 135 μm, 140 μm, 145 μm, 150 μm, 155 μm, 160 μm, 165 μm, 170 μm, 175 μm, 180 μm, 185 μm, 190 μm, 195 μm, 200 μm, 210 μm, 215 μm, 220 μm, 225 μm, 230 μm, 235 μm, 240 μm, 245 μm, 250 μm, 255 μm, 260 μm, 265 μm, 270 μm, 275 μm, 280 μm, 285 μm, 290 μm, 295 μm, 300 μm, 310 μm, 315 μm, 320 μm, 325 μm, 330 μm, 335 μm, 340 μm, 345 μm, 350 μm, 355 μm, 360 μm, 365 μm, 370 μm, 375 μm, 380 μm, 385 μm, 390 μm, 395 μm, 400 μm, 410 μm, 415 μm, 420 μm, 425 μm, 430 μm, 435 μm, 440 μm, 445 μm, 450 μm, 455 μm, 460 μm, 465 μm, 470 μm, 475 μm, 480 μm, 485 μm, 490 μm, 495 μm, 500 μm, 510 μm, 515 μm, 520 μm, 525 μm, 530 μm, 535 μm, 540 μm, 545 μm, 550 μm, 555 μm, 560 μm, 565 μm, 570 μm, 575 μm, 580 μm, 585 μm, 590 μm, 595 μm, 600 μm, 610 μm, 615 μm, 620 μm, 625 μm, 630 μm, 635 μm, 640 μm, 645 μm, 650 μm, 655 μm, 660 μm, 665 μm, 670 μm, 675 μm, 680 μm, 685 μm, 690 μm, 695 μm, 700 μm, 710 μm, 715 μm, 720 μm, 725 μm, 730 μm, 735 μm, 740 μm, 745 μm, 750 μm, 755 μm, 760 μm, 765 μm, 770 μm, 775 μm, 780 μm, 785 μm, 790 μm, 795 μm, 800 μmm, 810 μm, 815 μm, 820 μm, 825 μm, 830 μm, 835 μm, 840 μm, 845 μm, 850 μm, 855 μm, 860 μm, 865 μm, 870 μm, 875 μm, 880 μm, 885 μm, 890 μm, 895 μmm, 900 μm, 910 μm, 915 μm, 920 μm, 925 μm, 930 μm, 935 μm, 940 μm, 945 μm, 950 μm, 955 μm, 960 μm, 965 μm, 970 μm, 975 μm, 980 μm, 985 μm, 990 μm, 995 μm, 1000 μm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, and including all the thickness to the one decimal place between about 0.1 μm-about 5 mm.

The present invention can be defined in any of the following numbered paragraphs:

[1] A method of producing matrix vesicle calcification, the method comprising: (a) raising the pH of collagen stored or prepared in an acidic solution, thereby causing the collagen to come out of the acidic solution to form a mesh-like network; and (b) adding matrix vesicles to the collagen network, resulting in calcification.

[2] A method for visualizing g matrix vesicle calcification, the method comprising: (a) raising the pH of collagen stored or prepared in an acidic solution, thereby causing the collagen to come out of the acidic solution to form a mesh-like network; (b) adding matrix vesicles to the collagen network, resulting in calcification; and (c) imaging the calcification.

[3] The method of paragraph 1 or 2, wherein the calcification is micro-, macro- or a combination of micro and macro calcifications.

[4] The method of any one of paragraphs 1-3, wherein the calcification is imaged in real time.

[5] The method of any one of paragraphs 1-4, wherein the calcifications are imaged in 3D.

[6] The method of any one of paragraphs 2-5, wherein the imaging is via confocal microscopy or reflected light microscopy.

[7] The method of any one of paragraphs 1-6, wherein the imaging comprises fluorescence.

[8] The method of any one of paragraphs 1-7, wherein the acidic solution of the collagen is acetic acid.

[9] The method of paragraph 8, wherein the acetic acid is about 0.1 M-about 0.5 M acetic acid.

[10] The method of any one of paragraphs 1-9, wherein the collagen is in a concentration range from about 0.1 mg/ml to about 5 mg/ml.

[11] The method of paragraph 10, wherein the concentration of the collagen is about 3.0 mg/ml to about 5.0 mg/ml.

[12] The method of paragraph 10, wherein the concentration of the collagen is about 0.1 mg/ml to about 3.0 mg/ml.

[13] The method of any one of paragraphs 1-12, wherein the collagen is selected from the group consisting of human collagen, bovine collagen or porcine collagen.

[14] The method of any one of paragraphs 1-13, wherein the collagen is selected from the group consisting of Type 1 collagen, Type II collagen, Type III collagen, Type IV collagen, or Type V collagen.

[15] The method of any one of paragraphs 1-14, wherein the collagen is a mixture of the group of collagen selected from Type 1, Type II, Type III, Type IV, and Type V collagen.

[16] The method of any one of paragraphs 1-15, wherein the collagen is human Type 1 collagen.

[17] The method of any one of paragraphs 1-16, wherein the pH of the collagen is raised to between about 7.0 and about 9.0.

[18] The method of paragraph 17, wherein the pH of the collagen is raised to 7.4.

[19] The method of paragraph 17 or 18, wherein the pH of the collagen is raised by adding an alkaline solution to the acidic collagen solution.
[20] The method of paragraph 19, wherein the alkaline solution is sodium or potassium hydroxide.
[21] The method of any one of paragraphs 1-20, wherein the matrix vesicles are prepared from smooth muscle cells, macrophages, valvular interstitial cells, fibroblasts, osteoblasts, mesenchymal stem cell, or any other cell that is known to deposit calcific mineral.
[22] The method of any one of paragraphs 1-21, wherein the matrix vesicles are labeled prior to adding to the collagen network.
[23] The method of any one of paragraphs 1-22, wherein the matrix vesicles are fluorescently labeled prior to adding to the collagen network.
[24] The method of any one of paragraphs 1-23, further comprising adding dyes to the calcifications, thereby facilitating the visualization/imaging of the calcifications.
[25] The method of paragraph 24, wherein the dye is a fluorescent dye.
[26] The method of paragraph 25, wherein the fluorescent dye is a traditional or near-infrared fluorescent dye.
[27] The method of any one of paragraphs 24-26, wherein the dye labels the matrix vesicles added.
[28] The method of any one of paragraphs 1-27, further comprising adding a reagent to the calcification to determine its effect on the calcifications.
[29] The method of any one of paragraphs 1-28, wherein the reagent is bisphosphonate.
[30] A method of screening for agents that modulate the calcifications in unstable plaques comprising providing a collagen hydrogel/matrix vesicle calcification system, adding a test agent or a control test agent and imaging the calcification.
[31] The method of paragraph 30, wherein the collagen hydrogel/matrix vesicle calcification system is produced by raising the pH of collagen stored or prepared in an acidic solution, thereby causing the collagen to come out of the acidic solution to form a mesh-like network; and adding matrix vesicles to the collagen network, thereby resulting in calcification.
[32] The method of paragraph 30 or 31, wherein the control test agent is a buffer or a cell culture medium.
[33] The method of any one of paragraphs 30-32, wherein the modulation can be promoting calcification or inhibiting calcification.
[34] The method of any one of paragraphs 30-33, further comprising determining that the test agent is promoting calcification when calcification occurs faster compared to the control test agent.
[35] The method of any one of paragraphs 30-35, further comprising determining that the test agent is inhibiting calcification when calcification occurs slower compared to the control test agent.
[36] The method of paragraph 34 or 35, wherein the faster or slower is at least 5% compared to the control test agent.

Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This disclosure is further illustrated by the following example which should not be construed as limiting. The contents of all references cited throughout this application, as well as the figures and table are incorporated herein by reference.

EXAMPLES

Example 1

Figure 1B:
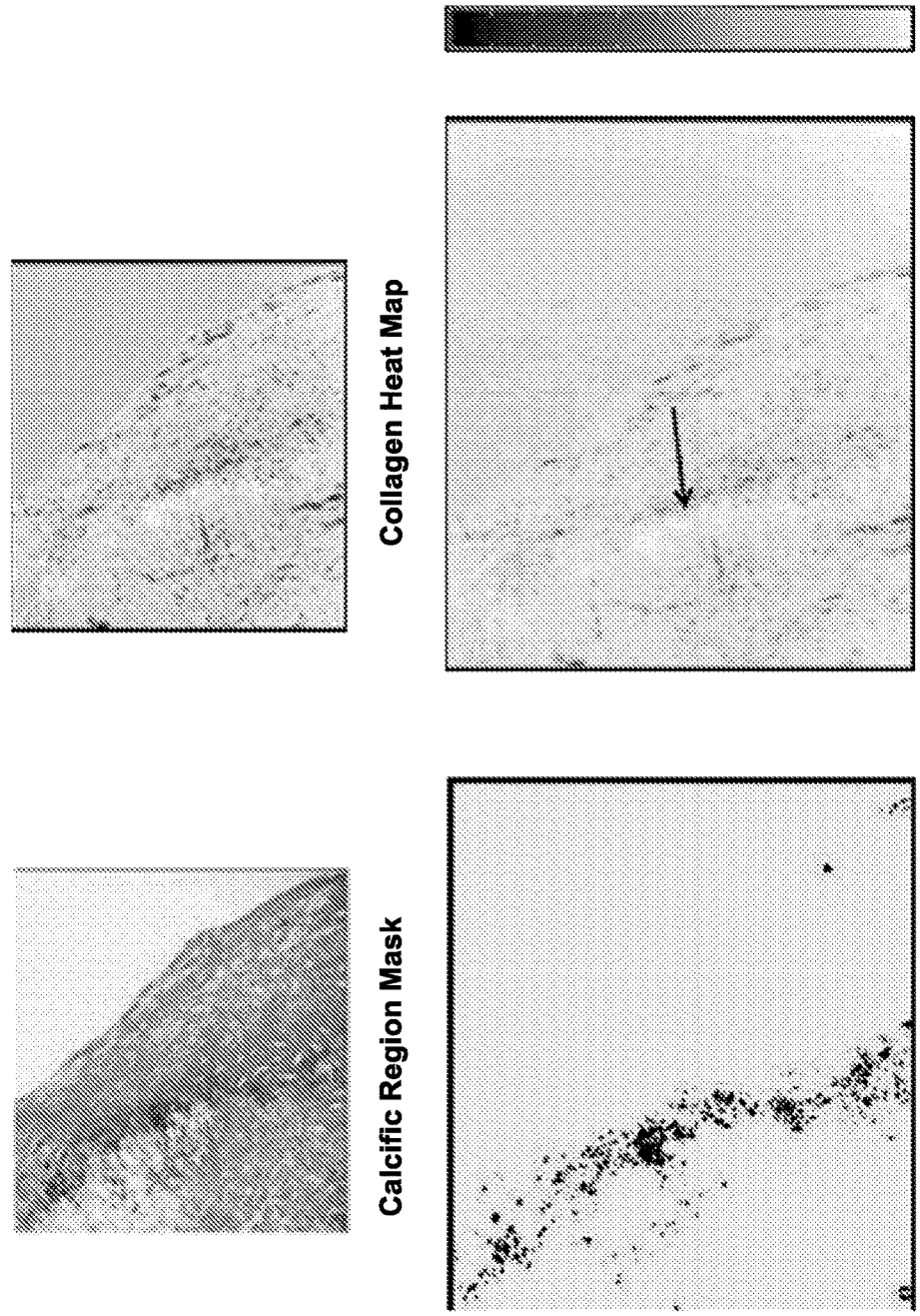
FIG. 1B illustrates a calcific region mask and collagen heat map. Invented images are shown.

FIG. 1A shows calcifications and collagen in mouse and human arteries. Von Kossa (calcification) and picrosirius red (collagen) staining of ApoE−/− mouse and human arteries clearly reveal thick collagen borders around macrocalcifications and microcalcifications that are observed in regions of low collagen density. FIG. 1B illustrates the calcific region mask and collagen heat map.

Figure 2A:
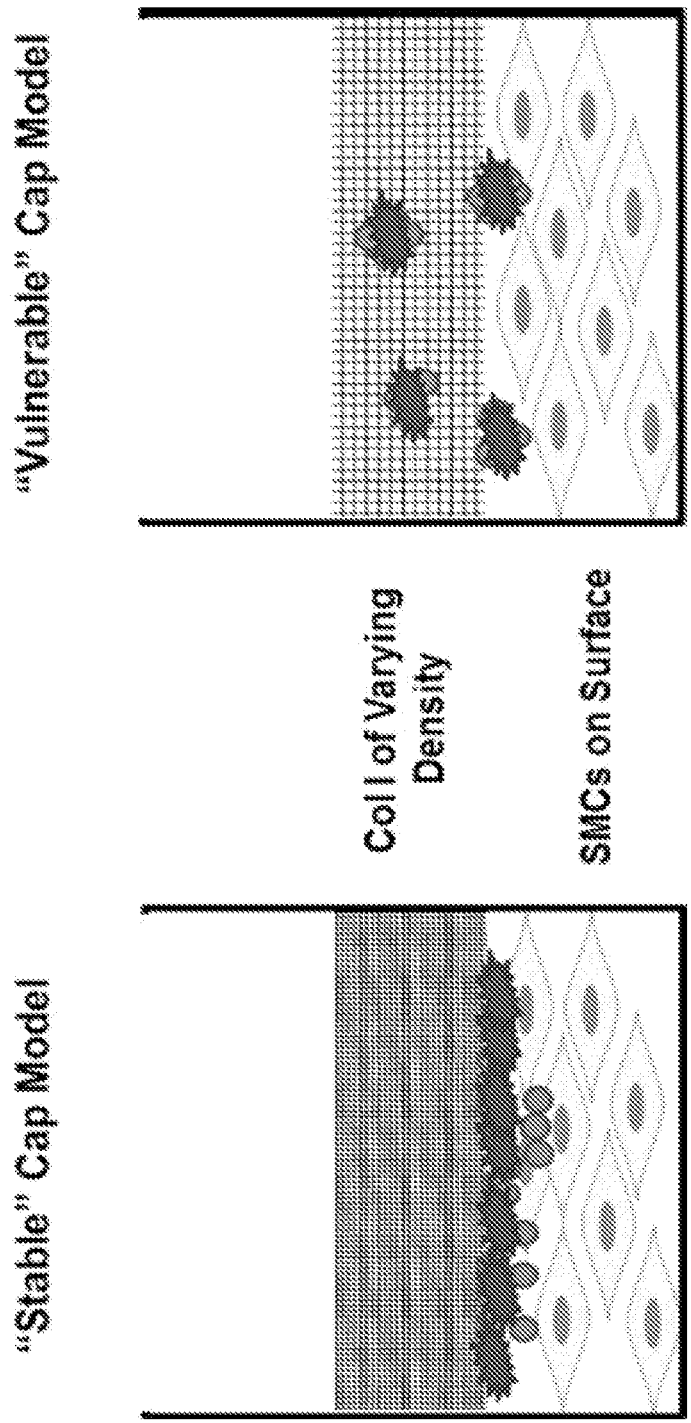
FIG. 2A illustrates a stable cap model and vulnerable cap model. Synthetic collagen hydrogels were added to human coronary artery smooth muscle cells (SMCs) cultured in normal or osteogenic conditions (DMEM with 10 nM dexamethasone, 100 µM L-ascorbic acid, and 10 mM β-glycerol phosphate). Hydrogels with a high density of collagen were used to simulate a stable fibrous cap, and collagen poor hydrogels were used to simulate a vulnerable fibrous cap.

In one example, synthetic collagen hydrogels of embodiments of the invention were added to human coronary artery smooth muscle cells (SMCs) cultured in normal or osteogenic conditions. In one embodiment, normal conditions consisted of Dulbecco's Modified Eagle's Medium supplemented with 10% by volume fetal bovine serum and 1% by volume penicillin/streptomycin. In one embodiment, osteogenic conditions were prepared by supplementing this normal medium with 10 nmol/L dexamethasone, 100 µmol/L L-ascorbic acid, and 10 mmol/L β-glycerolphosphate. Hydrogels created with a high density of collagen were used to simulate a stable fibrous cap, and collagen poor hydrogels were used to simulate a vulnerable fibrous cap. In this example, the collagen in the solution was diluted to different starting concentrations prior to raising the pH to control the density of collagen. The stable cap model led to an increase in greater amount of calcification beneath the collagen hydrogels compared to formation of micro-calcifications in the vulnerable cap model, as shown in FIGS. 2A and 2B.

Figure 3A:
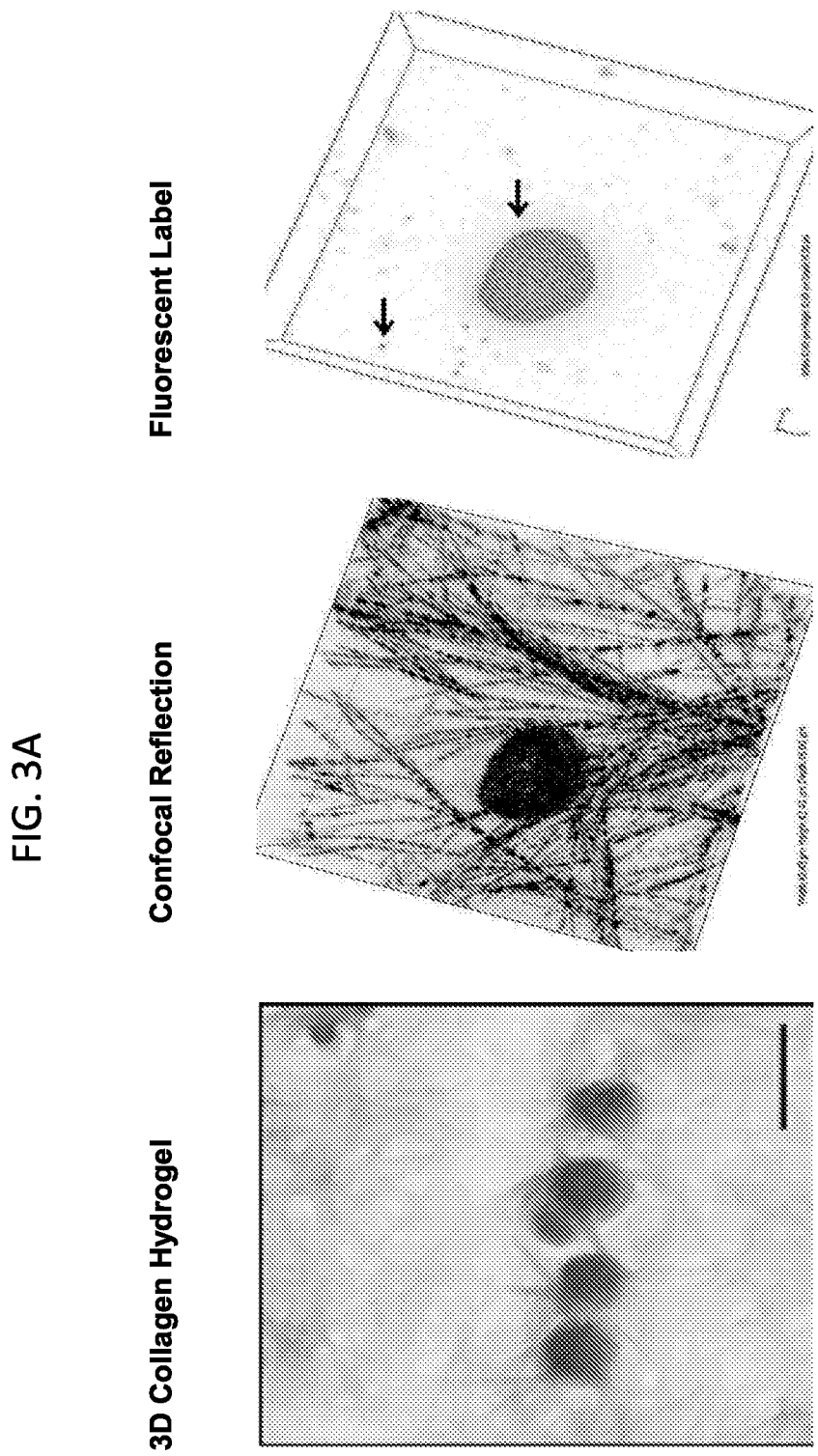
FIG. 3A illustrates micro-calcification structures forming within the 3D collagen hydrogel system according to an embodiment of the invention. Confocal reflection microscopy indicates that the structures are situated between collagen fibers within the hydrogels and can be labeled with fluorescent dyes. Invented images are shown.
Figure 3B:
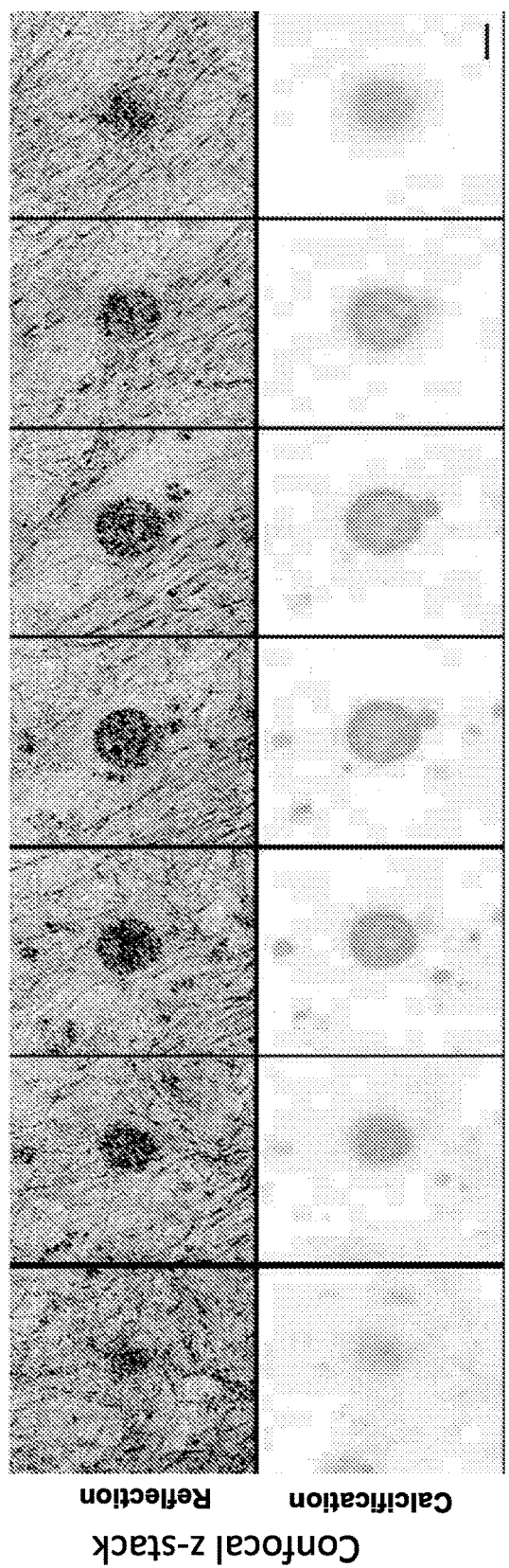
FIG. 3B illustrates a confocal z-stack. Calcification within the matrix vesicle aggregate structures was identified using a near-infrared calcium phosphate tracer in a confocal z-stack. Scale bar=5 µm. Invented images are shown.

A recent study illustrated the pervasiveness of spherical microcalcifications throughout human arterial plaques. Similar microcalcification structures forming within the 3D collagen hydrogel system can be seen in FIG. 3A. In this experiment, the media supernatant containing matrix vesicles was removed from SMCs cultured in osteogenic conditions and this supernatant was added to the collagen hydrogel system. The arrows indicate small, less than 500 nm, and large, about 5 µm, matrix vesicle aggregates. Confocal reflection microscopy indicates that the structures are situated between collagen fibers within the hydrogels and can be labeled with fluorescent dyes for added resolution and sensitivity. Calcification within the structures was identified using a near-infrared calcium phosphate tracer using in a confocal microscope. A confocal z-stack is shown in FIG. 3B. These techniques can be used to monitor changes in matrix vesicle calcification, and to test the ability of compounds to prevent matrix vesicle aggregation and/or calcification.

Figure 4A:
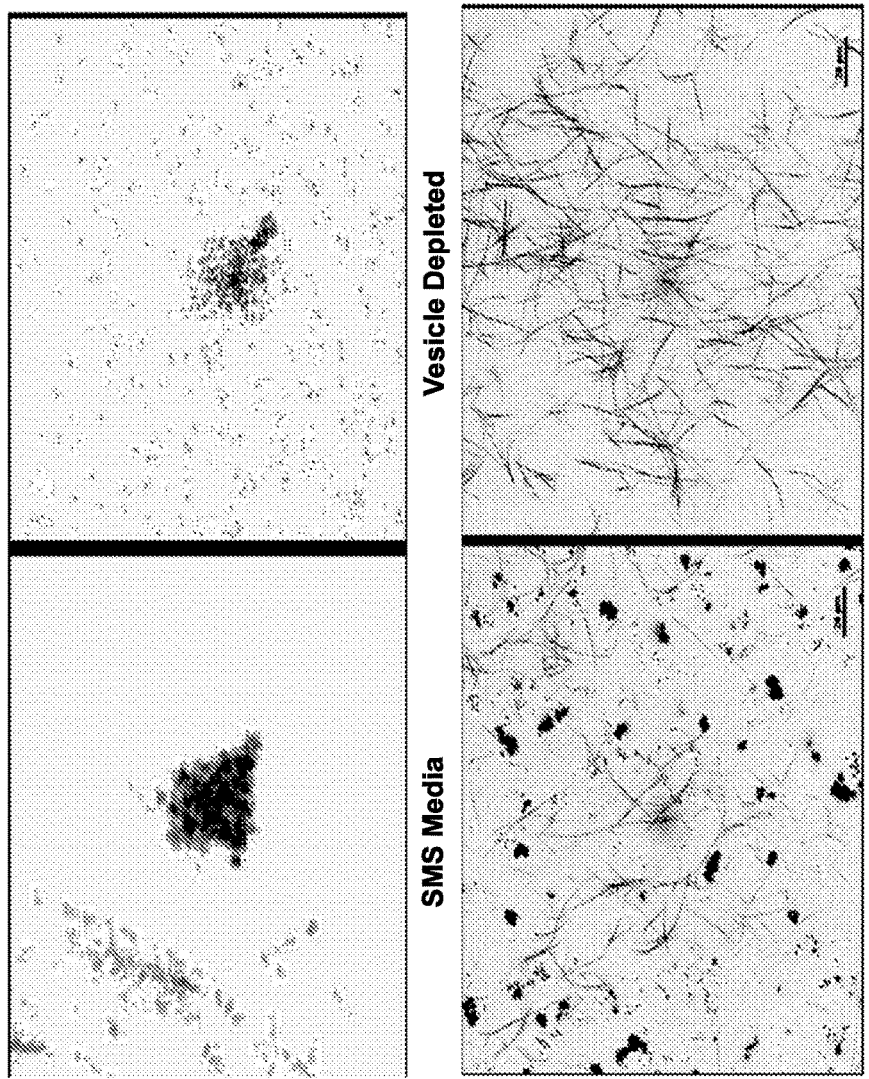
FIG. 4A illustrates vesicles that will become calcified (top), and a lack of vesicles (bottom). CellLight plasma membrane probe confirmed that the structures identified within the gels were cellular derived. Following ultracentrifugation depletion of matrix vesicles from SMC conditioned media, micro-calcifications were no longer observed. Invented images are shown.
Figure 4B:
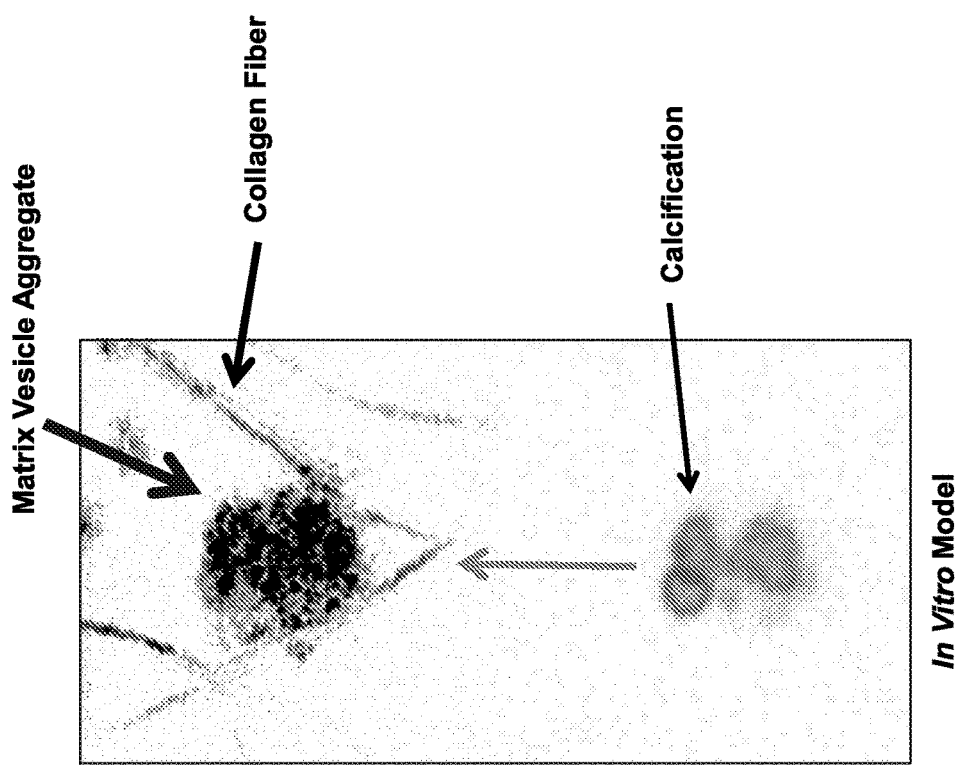
FIG. 4B is an in vitro image illustrating a matrix vesicle aggregate, collagen fiber and calcification. Micro-calcifications form by matrix vesicle aggregation within the collagen hydrogel that resemble those observed from tissue. The size of the aggregates was inversely proportional to the collagen density within the hydrogels. Invented images are shown.
Figure 4D:
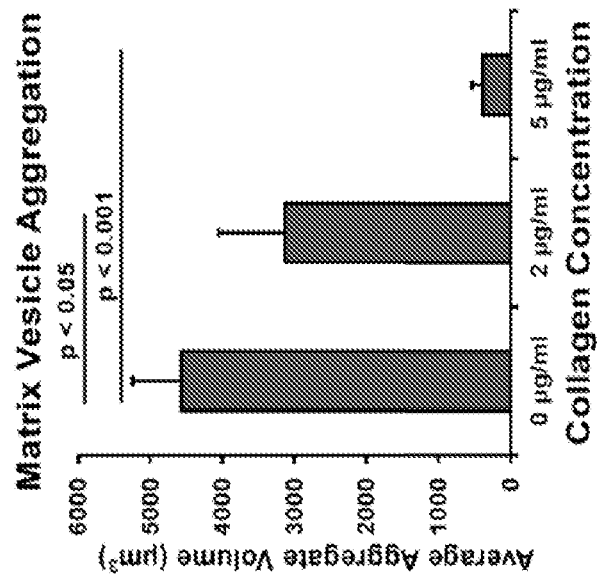
FIG. 4D is a bar graph illustrating the relationship between collagen concentration and average aggregate volume of matrix vesicles.
Figure 4C:
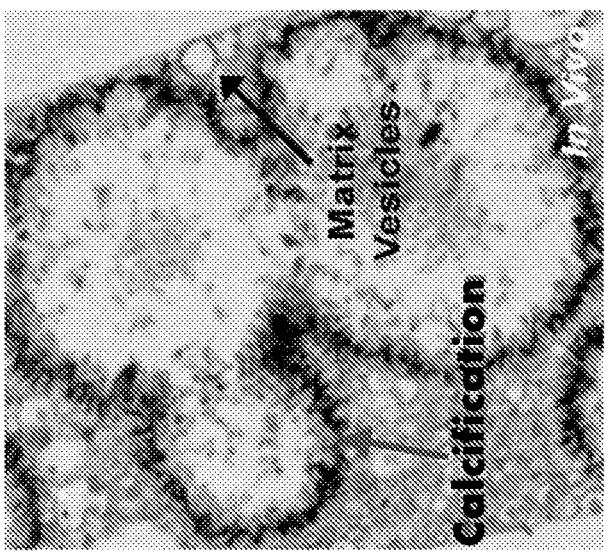
FIG. 4C is an in vivo image illustrating matrix vesicles and calcifications.
Figure 4E:
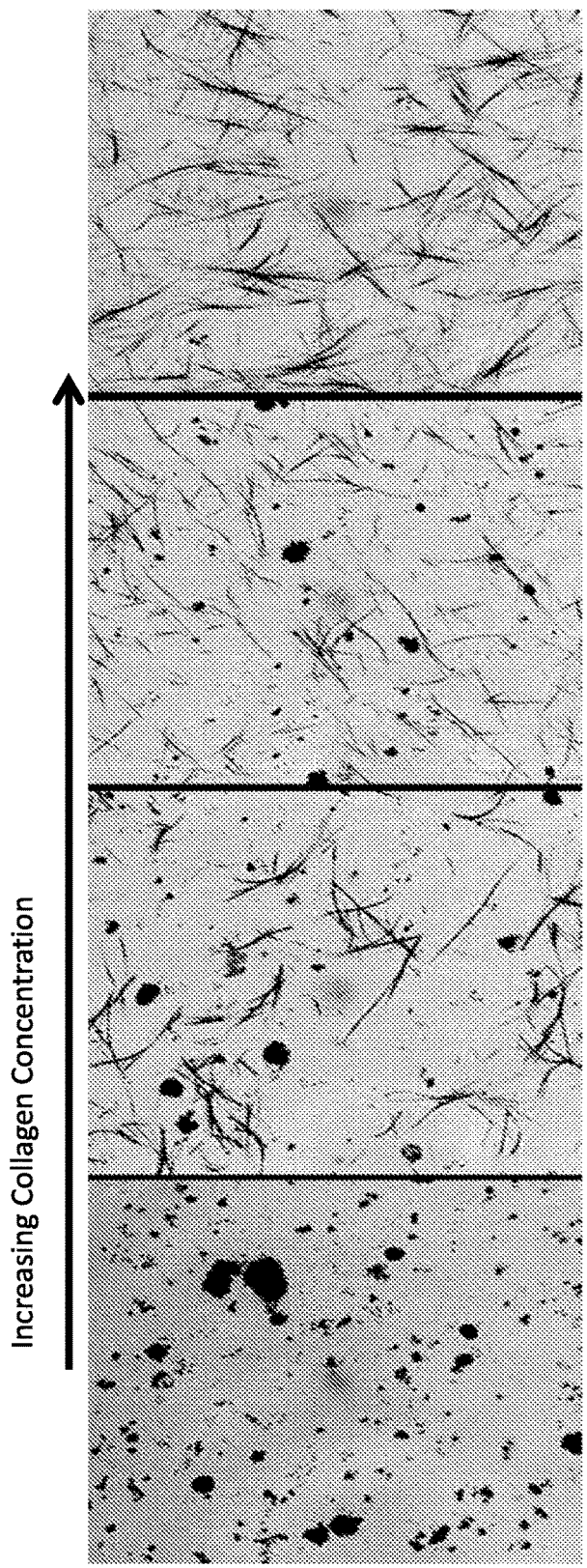
FIG. 4E illustrates the reducing size of matrix vesicle aggregation as collagen concentration is increased. Images show that the size of matrix vesicle aggregates was inversely proportional to the collagen density within the hydrogels. Invented images are shown.

A CellLight® plasma membrane probe confirmed that the structures identified within the gels were cellular derived. Following ultracentrifugation depletion of matrix vesicles from smooth muscle cells (SMC), micro-calcifications were no longer observed, as shown in FIG. 4A. Thus, the detected structures were identified as aggregates of matrix vesicles. In vitro and in vivo models illustrating aggregates of matrix vesicles are shown in FIGS. 4B and 4C, respectively. The diameter of the aggregates was inversely proportional to the collagen density within the hydrogels created according to embodiments of the invention, as shown in FIGS. 4D and 4E.

Figure 5A:
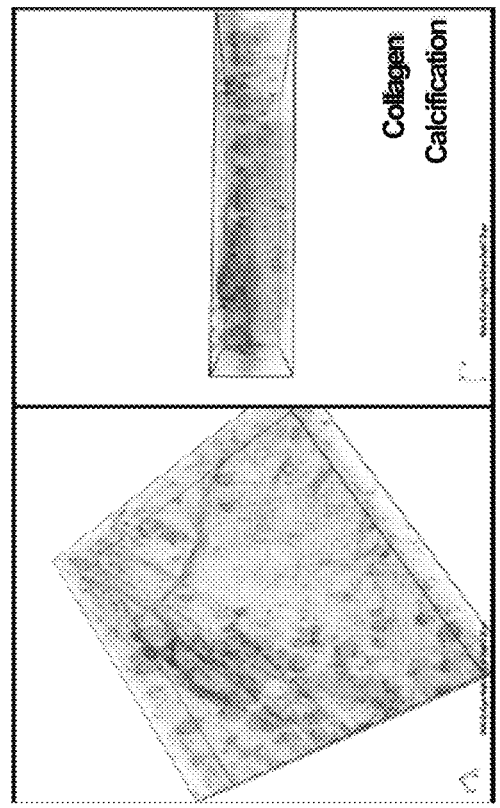
FIG. 5A illustrates calcifications observed in vitro after sequestering the matrix vesicles. Invented images are shown.
Figure 5B:
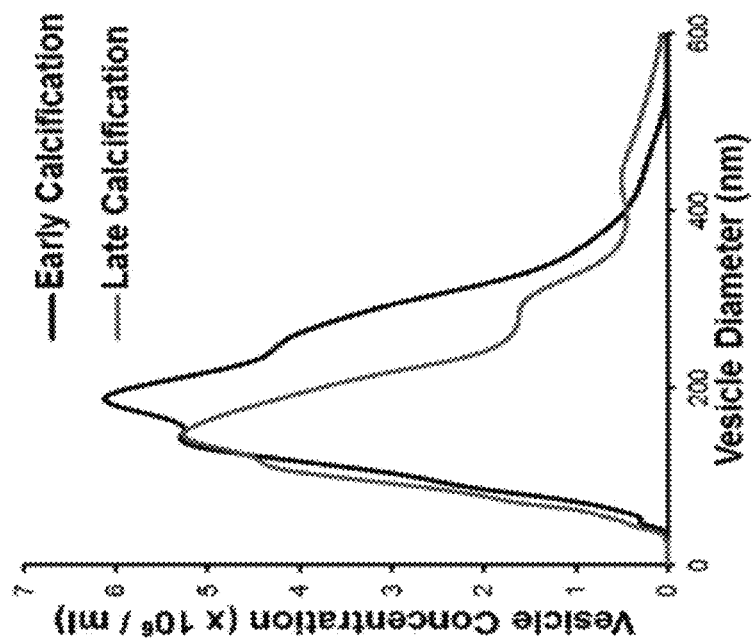
FIG. 5B illustrates vesicle concentration as a function of vesicle diameter for early and late calcification.

SMCs cultured in osteogenic conditions recapitulated collagen accumulation and calcification. Osteogenic conditions were prepared by supplementing normal growth medium with 10 nmol/L dexamethasone, 100 µmol/L L-ascorbic acid, and 10 mmol/L β-glycerolphosphate. After 14 days of culture in osteogenic conditions, SMCs produced a collagen matrix that entrapped underlying calcification. Similarly, nanoparticle tracking analyses indicated a decrease in the matrix vesicles measured in the conditioned media of calcific SMCs over the course of calcification, as shown in FIG. 5B. Thus, these vesicles may be sequestered by the newly formed collagen matrix, resulting in the calcification observed in vitro, as shown in FIG. 5A. FIG. 5B illustrates vesicle concentration as a function of vesicle diameter for early and late calcification.

Figure 6A:
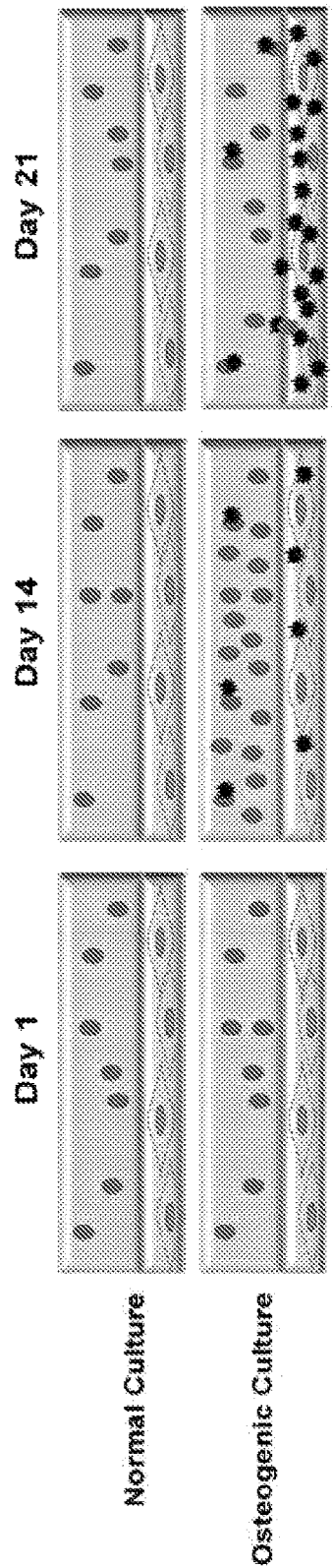
FIGS. 6A-6C illustrate the changes in protein expressed in smooth muscle cells and matrix vesicles in normal and osteogenic conditions over a period of 21 days.
Figure 6B:
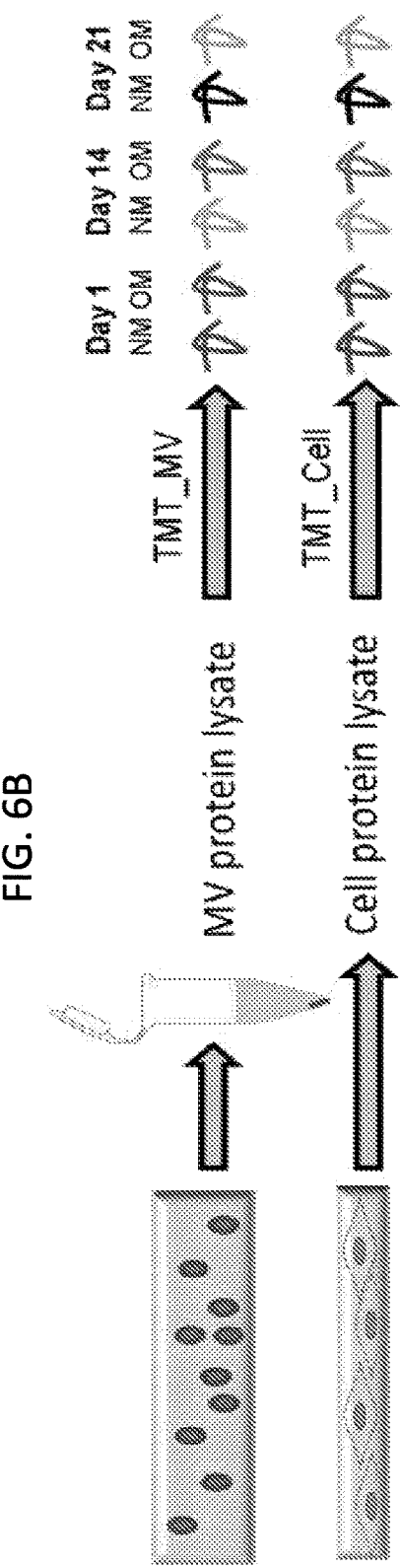
Figure 6C:
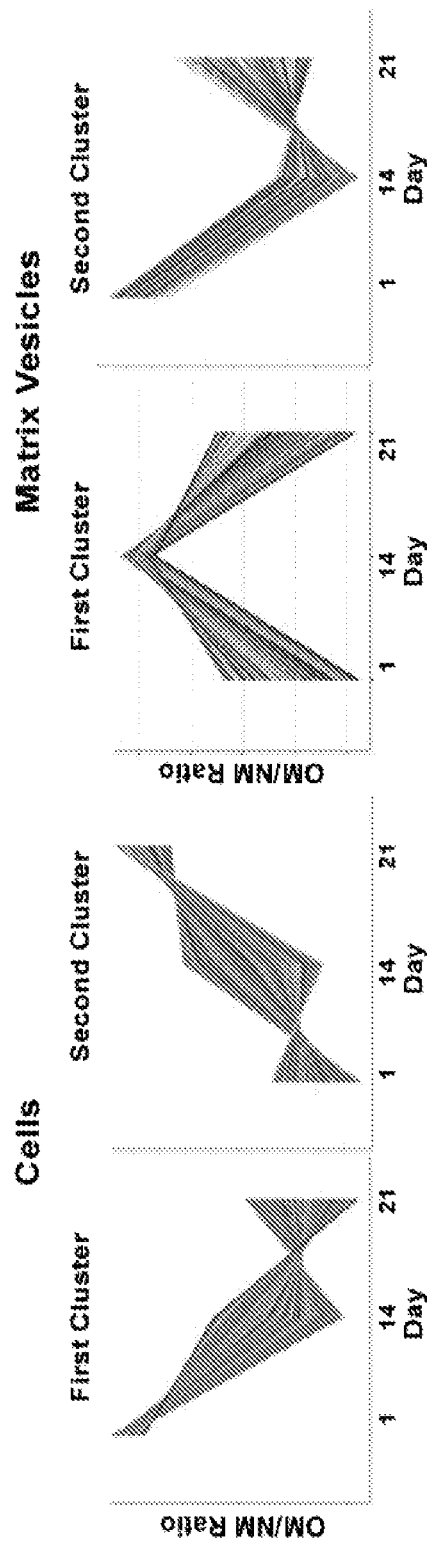
Figure 6D:
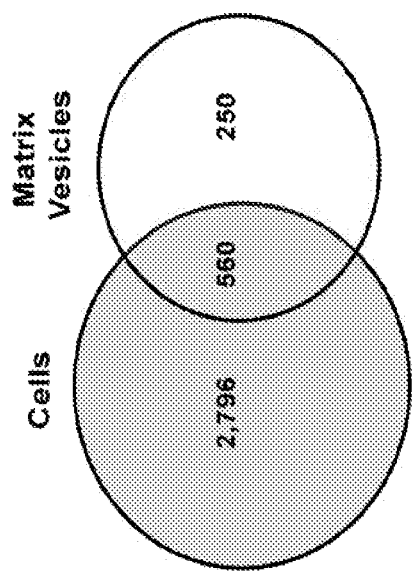
FIG. 6D illustrates the subset of proteins identified in the smooth muscle cells and matrix vesicles.

Mass spectrometry revealed phenotypic changes in calcifying matrix vesicles. Tandem mass tagging was used to monitor changes in protein expressed in SMCs and matrix vesicles in normal and osteogenic conditions over a period of 21 days. The results are shown in FIGS. 6A-6C. A subset of proteins was identified in only matrix vesicles as shown in FIG. 6D, indicating that these proteins are enriched in the vesicles. Clusterization of proteins based upon temporal changes revealed phenotypic changes in SMCs; however, matrix vesicles revealed specific peaks in protein expression that could be indicative of the onset of calcification of these vesicles, as shown in FIG. 6C.

As shown in FIG. 7A, a stable fibrous cap with high collagen density led to matrix vesicle aggregation beneath the cap, and the formation of large calcifications or macro-calcification. In FIG. 7B, a vulnerable fibrous cap modeling with localized collagen degradation due to inflammation led to matrix vesicle aggregation within the cap, and the formational of micro-calcifications. Thus, collagen in the hydrogel system controls the aggregation of calcifying matrix vesicles. This aggregation event is crucial to the development of micro-calcifications. In other words, the formation of micro-calcifications is inseparable from a reduction of collagen within the fibrous cap.

Figure 8:
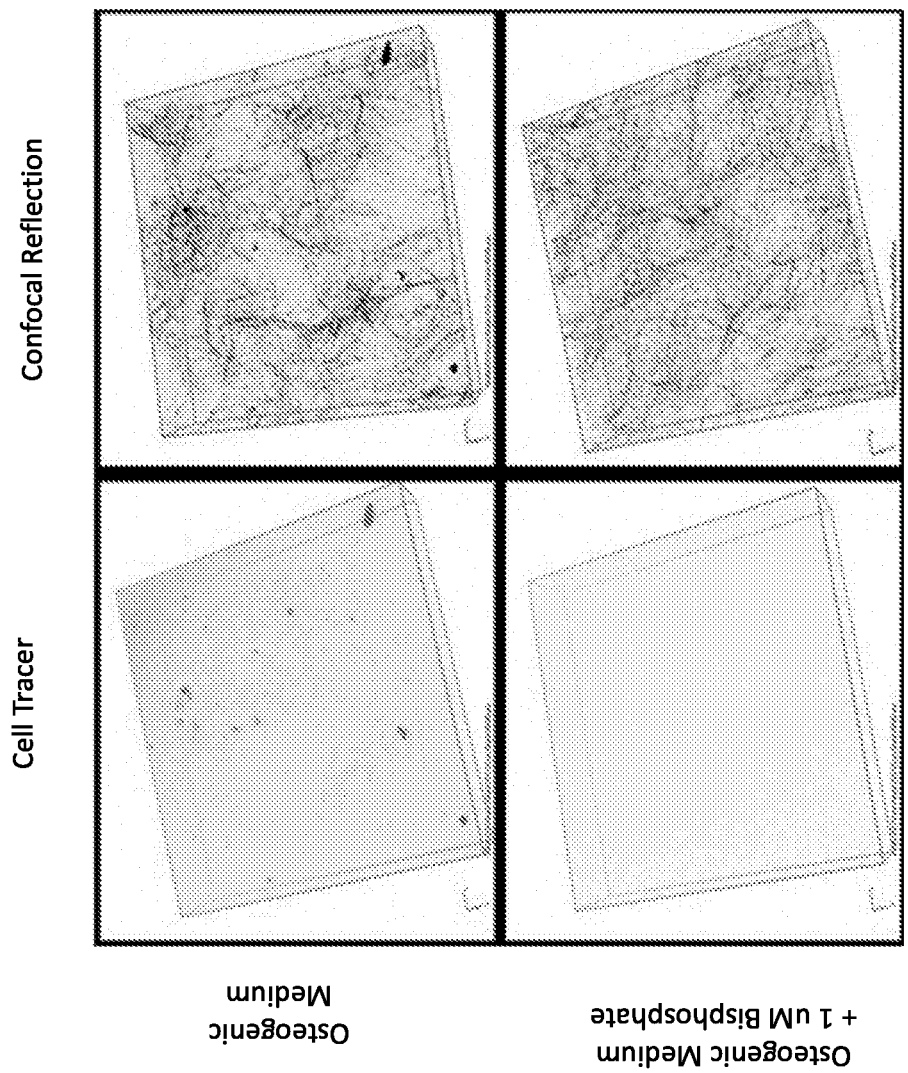
FIG. 8 illustrates representative 3-dimensional reconstructions of hydrogels with calcifying matrix vesicles and the same vesicles treated with bisphosphonate. Invented images are shown.
Figure 9:
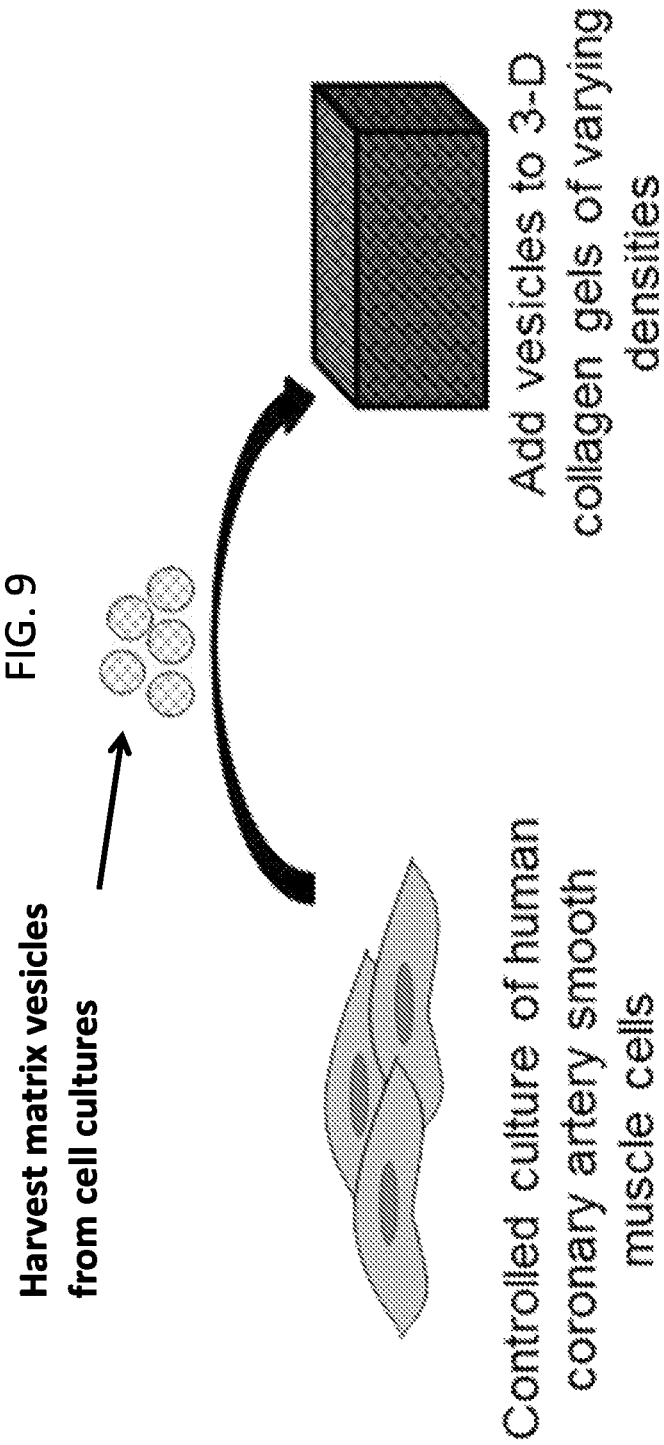
FIG. 9 illustrates the method of producing the matrix vesicle/calcification system. Matrix vesicles were isolated from calcifying smooth muscle cells and placed into a hydrogel model of the fibrous cap.
Figure 10:
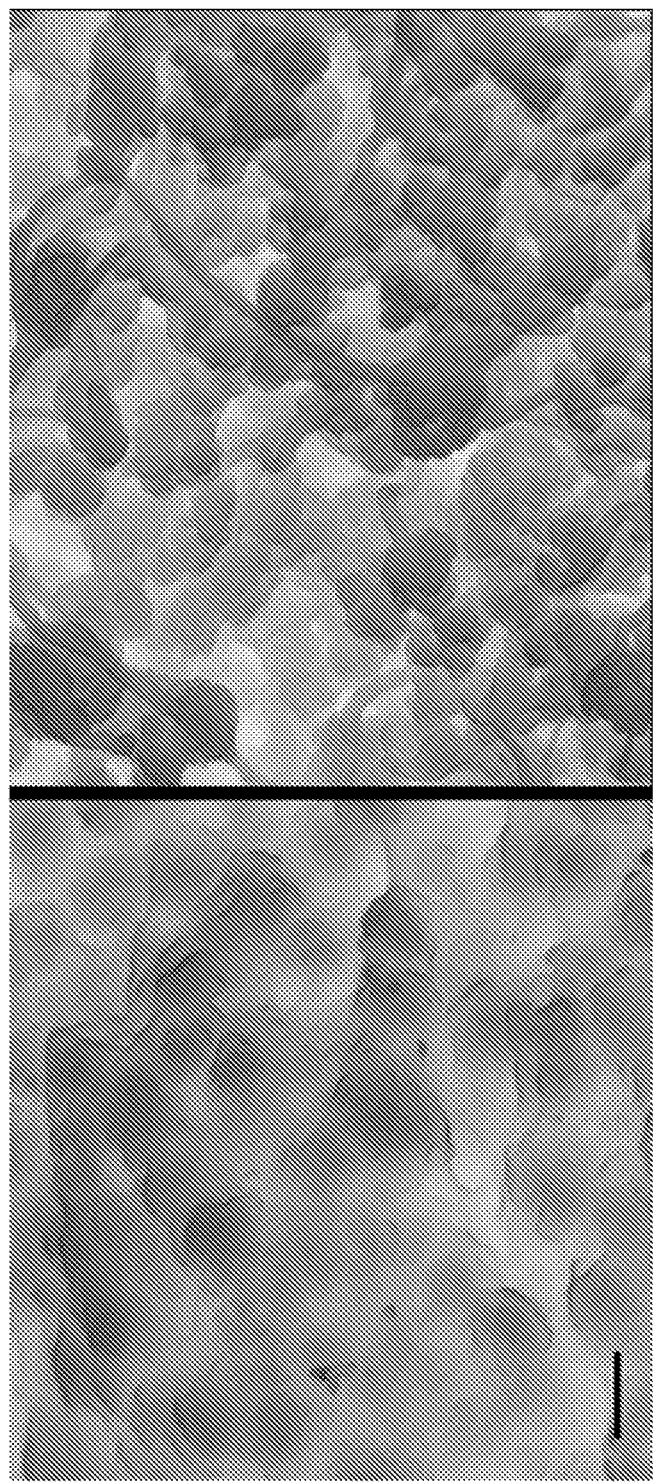
FIG. 10 illustrates scanning electron micrographs showing spherical structures composing calcifications throughout human arterial plaques. The inventors have identified similar calcification structures forming within the disclosed matrix vesicle/calcification system comprising 3D collagen hydrogel.
Figure 11:
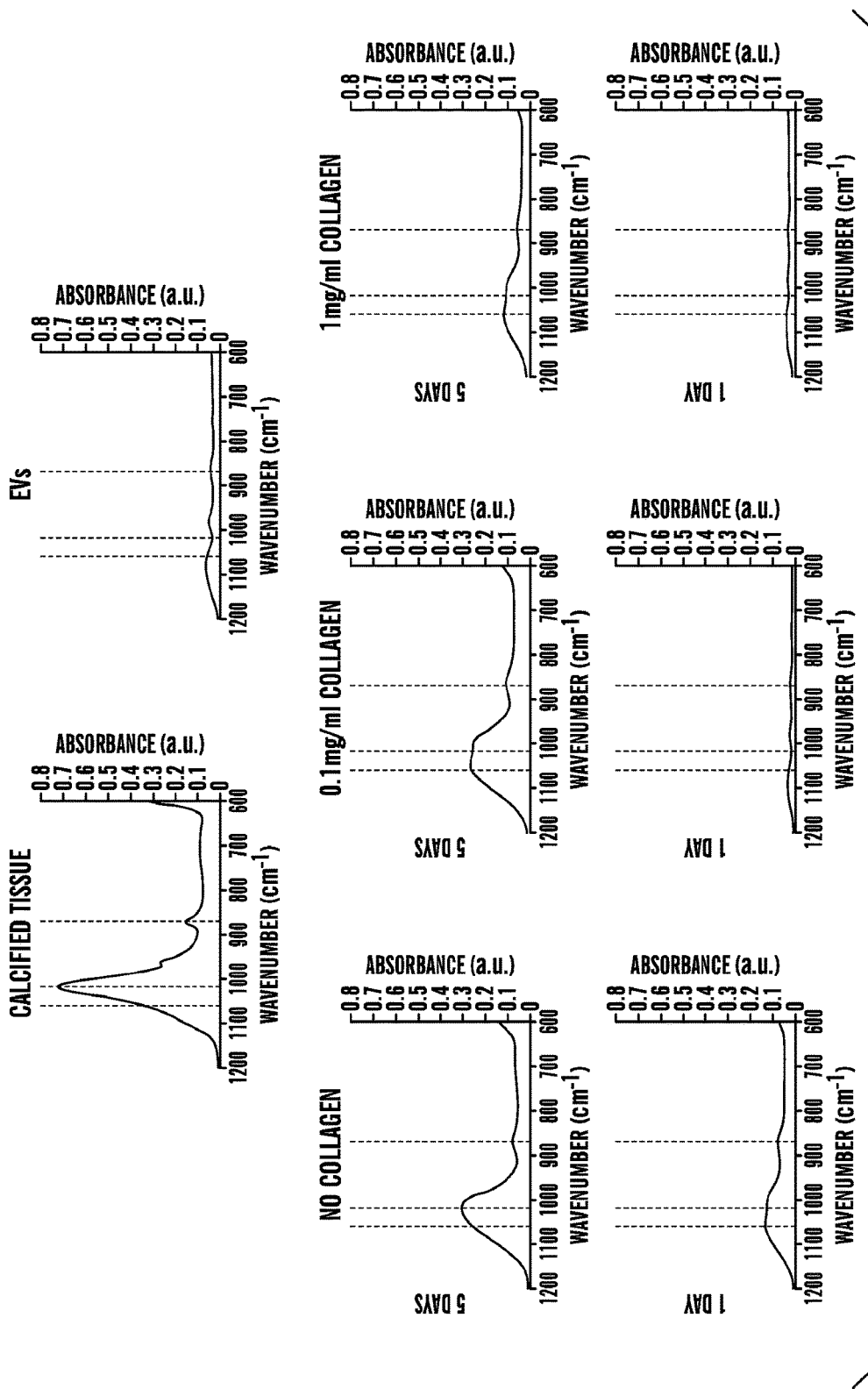
FIG. 11 illustrates a Fourier transform analysis of phosphate mineral showing that in matrix vesicle/calcification system, mineral matures to resemble that formed in calcified tissue. The maturation rate is inversely proportional to collagen density.

In order to prove that the aggregation of matrix vesicles resulting in micro-calcifications could be mediated by the actual nucleation of calcium phosphate on the matrix vesicle membranes, bisphosphonate treatments to prevent calcium phosphate growth were used on the hydrogels to determine if the aggregation and calcification processes can be inhibited. FIG. 8 illustrates representative 3D reconstructions of hydrogels with calcifying matrix vesicles and the same vesicles treated with bisphosphonate. In this experiment, the media supernatant containing matrix vesicles was removed from SMCs cultured in osteogenic conditions and this supernatant was added to the collagen hydrogel system with or without 1 µM bisphosphonate. Aggregation of matrix vesicles is are observed in the samples not treated with bisphosphonate; however, the bisphosphonate treated group did not exhibit matrix vesicle aggregation within the collagen hydrogels. These results indicate that matrix vesicle aggregation observed in osteogenic media samples is inhibited by the addition of 1 µM bisphosphonate to the hydrogel system. These results are cellular-independent.

In this experiment, the matrix vesicles were isolated from the SMCs and divided into two portions. One portion was added directly to the hydrogels, and one portion received bisphosphonate prior to being added to the hydrogels. Cell tracer was then added to the gels to visualize the formation of vesicular aggregates (green fluorescence). These results demonstrate the potential for this 3D hydrogel system as a tool for screening changes in matrix vesicle aggregation, the driving force behind the formation of micro-calcifications.

Example 2

Collagen Preparation

Collagen hydrogels are made by slowly raising the pH of collagen stored in a solution of acetic acid. At higher pH, the collagen comes out of solution to form a network. A volume of the collagen stock is added and mixed with ice cold cell culture media to produce the desired final collagen concentration (usually between 0.1 and 5 mg/ml). The pH of this solution should be measured, and very small amounts of 5 N sodium hydroxide should be added until the solution is between pH 7.0 and 9.0. If the solution exceeds this pH, the solution should be discarded and the procedure must be started from the beginning Once the pH is correct, the mixed collagen solution should be added to chambered cover-glass wells (200-300 µl is appropriate for each well of an 8-well chamber). In order to image the gels, the cover-glass should be #1.5 borosilicate. If desired, cells can be cultured on the chambers prior to the introduction of the collagen hydrogel solution. The chambers with collagen hydrogel solution should be incubated at 37° C. for at least 1 hour to let the collagen network form.

For experiments in which cells were not cultured on the chambers prior to the introduction of the hydrogel solution, after the hydrogel networks have formed fluorescently labeled or unlabeled extracellular matrix vesicles can be added to this collagen network (the volume added should be equal to the volume of hydrogel in the chamber well), and the resulting aggregation and calcification processes can be imaged by confocal fluorescence and reflection microscopy.

Preparation of Matrix Vesicles

Matrix vesicles should be collected by adding culture medium with no more than 0.1% fetal bovine serum to the cells of interest. After 24 h, this medium should be collected and centrifuged at 1,000×g for 5 min to pellet large cell debris. The vesicles of interest are in the supernatant following this centrifugation. To label matrix vesicles with fluorescent Cell Tracker dyes, dilute the dye in dimethyl sulfoxide per the manufacturer's recommendation. Add 0.25 µl of this dye stock solution per 1 ml of vesicles to be labeled. Incubate the vesicles with the dye at 37° C. for 30 min. After this incubation period excess fluorescent dye should be removed by either ultracentrifugation or column separation methods. For ultracentrifugation, pellet the vesicles at 100,000×g for 40 min and resuspend the vesicles in 1 ml of PBS. Repeat this process twice. After the final ultracentrifugation, resuspend the vesicles in cellular growth medium. These resuspended vesicles can then be added to the wells containing the collagen hydrogels.

For column-based dye separation, the vesicles/dye solution should be run through columns per manufacturer's protocol (GE Healthcare PD-10 columns have been used successfully). After the vesicle portion is collected from the column, the vesicles should be pelleted by ultracentrifugation at 100,000×g for 40 min and resuspended in cellular growth medium. These resuspended vesicles can then be added to the wells containing the collagen hydrogels. After the prescribed incubation time at 37° C., calcification can be detected using OsteoSense® 680 (a near-infrared calcium tracer). OsteoSense® stock solution can be made by adding 180 µl of PBS to the pre-packaged tube. This stock should be added to the collagen hydrogels such that the final concentration is 1 part OsteoSense® stock to 100 parts vesicles/hydrogel volume. Incubate the gels with the Osteo-Sense® stock overnight at 37° C.

If desired, the hydrogels can be imaged using an inverted microscope the following day by removing excess medium such that the hydrogels rest on the bottom of the chamber cover-glass.

The present invention has been described in relation to particular examples, which are intended in all respects to be illustrative rather than restrictive. Those skilled in the art will appreciate that many different combinations of materials and components will be suitable for practicing the present invention.

Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A method of screening for agents that modulate the calcifications in unstable plaques comprising:
   (a) providing a 3-dimensional (3-D) collagen hydrogel/matrix vesicle calcification system,
   (b) adding a test agent or a control test agent to the 3-D collagen hydrogel/matrix vesicle calcification system, and
   (c) imaging for calcification that has occurred within the 3-D collagen hydrogel calcification,
   wherein the 3-D collagen hydrogel/matrix vesicle calcification system is produced by raising the pH of collagen stored or prepared in an acidic solution, thereby causing the collagen to come out of the acidic solution to form a 3-D collagen hydrogel mesh-like network; and adding matrix vesicles to the network,
   and wherein the collagen is in a concentration range from about 0.1 mg/ml to about 5 mg/ml.

2. The method of claim 1, wherein the control test agent is a buffer or a cell culture medium.

3. The method of claim 1, wherein the modulation can be promoting calcification or inhibiting calcification.

4. The method of claim 1, further comprising determining that the test agent is promoting calcification when calcification occurs faster compared to the control test agent or determining that the test agent is inhibiting calcification when calcification occurs slower compared to the control test agent.

5. The method of claim 1, wherein the calcification occurring within the 3-D collagen/hydrogel is micro-calcification.

* * * * *